(12) United States Patent
Liu

(10) Patent No.: US 6,713,042 B2
(45) Date of Patent: Mar. 30, 2004

(54) ASCORBIC ACID ANALOGS FOR METALLORADIOPHARMACEUTICALS

(75) Inventor: Shuang Liu, Chelmsford, MA (US)

(73) Assignee: Bristol-Myers Squibb Pharma Company, Princeton, NJ (US)

(*) Notice: Subject to any disclaimer, the term of this patent is extended or adjusted under 35 U.S.C. 154(b) by 60 days.

(21) Appl. No.: 10/081,258

(22) Filed: Feb. 22, 2002

(65) Prior Publication Data

US 2002/0122769 A1 Sep. 5, 2002

Related U.S. Application Data

(60) Provisional application No. 60/271,389, filed on Feb. 26, 2001.

(51) Int. Cl.⁷ .................... A61K 51/00; A61M 36/14
(52) U.S. Cl. .................. 424/1.65; 424/1.11; 424/9.1; 548/400; 548/401; 549/200; 549/201
(58) Field of Search .................. 424/1.11, 1.65, 424/1.69, 1.49, 9.1; 530/300; 548/400, 401; 549/200, 201

(56) References Cited

U.S. PATENT DOCUMENTS

| | | | | |
|---|---|---|---|---|
| 4,504,462 A | * | 3/1985 | Van Duzee et al. | 424/1.11 |
| 4,707,353 A | * | 11/1987 | Bugaj et al. | 424/1.11 |
| 5,384,113 A | * | 1/1995 | Deutsch et al. | 424/1.69 |
| 5,985,240 A | * | 11/1999 | Zamora et al. | 424/1.69 |
| 6,066,309 A | | 5/2000 | Zamora et al. | 424/1.49 |
| 6,183,721 B1 | | 2/2001 | Albert et al. | 424/1.69 |
| 6,338,835 B1 | * | 1/2002 | Shochat et al. | 424/1.69 |

\* cited by examiner

*Primary Examiner*—Dameron L. Jones
(74) *Attorney, Agent, or Firm*—Blair Q. Ferguson; Paul D. Golian; Woodcock Washburn LLP

(57) ABSTRACT

The invention relates to the use of ascorbic acid analogs as buffering reagents and chelating agents for the preparation of metalloradiopharmaceuticals. Also, invention relates to the use of ascorbic acid as a buffering reagent, a chelating agent, and a stabilizer for the preparation and stabilization of radiopharmaceuticals and processes for making and using the same.

45 Claims, No Drawings

ASCORBIC ACID ANALOGS FOR METALLORADIOPHARMACEUTICALS

CROSS-REFERENCE TO RELATED APPLICATIONS

This application claims benefit to provisional application No. 60/271,389, filed Feb. 26, 2001.

FIELD OF THE INVENTION

This invention is related to the use of ascorbic acid analogs as buffering reagents and chelating agents for the preparation of metalloradiopharmaceuticals. This invention is particularly related to the use of ascorbic acid as a buffering reagent, a chelating agent, and a stabilizer for the preparation and stabilization of radiopharmaceuticals. This invention is also related to processes of making stable radiopharmaceutical compositions using ascorbic acid analogs as buffering agents, chelating agents, and stabilizers.

BACKGROUND

Radiopharmaceuticals are drugs containing a radionuclide. Radiopharmaceuticals are used routinely in nuclear medicine for the diagnosis or therapy of various diseases. They are typically small organic or inorganic compounds with a definite composition. They can also be macromolecules, such as antibodies or antibody fragments, that are not stoichiometrically labeled with a radionuclide. Radiopharmaceuticals form the chemical basis for the diagnosis and therapy of various diseases. The in vivo diagnostic information is obtained by intravenous injection of the radiopharmaceutical and determining its biodistribution using a gamma camera. The biodistribution of the radiopharmaceutical depends on the physical and chemical properties of the radiolabeled compound and can be used to obtain information about the presence, progression, and state of disease.

Radiopharmaceuticals can be divided into two primary classes: those whose biodistribution is determined exclusively by their chemical and physical properties; and those whose ultimate distribution is determined by their receptor binding or other biological interactions. The latter class is often called target-specific radiopharmaceuticals.

Metalloradiopharmaceuticals include a metallic radionuclide. A target-specific metalloradiopharmaceutical can be divided into four parts: a targeting molecule, a linker, a bifunctional Chelator (BFC), and a metallic radionuclide. The targeting molecule serves as a vehicle, which carries the radionuclide to the receptor site at the diseased tissue. The targeting molecules can be macromolecules such as antibodies or small biomolecules (BM), including peptides, peptidomimetics, and non-peptides. The choice of biomolecule depends upon the targeted disease or disease state. The radionuclide is the radiation source. The selection of metallic radionuclide depends on the intended medical use (e.g., diagnostic or therapeutic) of the target specific metalloradiopharmaceutical. The BFC is covalently attached to the targeting molecule either directly or through a linker and binds strongly to the metallic radionuclide via several coordination bonds. Selection of a BFC is largely determined by the nature and oxidation state of the metallic radionuclide. The linker can be a simple hydrocarbon chain or a long poly(ethylene glycol) (PEG) or a "naive" poly anionic or cationic peptide sequence, which is often used for modification of pharmacokinetics. Sometimes, a metabolizeable linker is used to increase the blood clearance and to reduce the background activity, thereby improving the target-to-background ratio.

The use of metallic radionuclides offers many opportunities for designing new radiopharmaceuticals by modifying the coordination environment around the metal with a variety of chelators. The coordination chemistry of the metallic radionuclide will determine the geometry of the metal chelate and the solution stability of the radiopharmaceutical. Different metallic radionuclides have different coordination chemistries, and require BFCs with different donor atoms and chelator frameworks. For "metal essential" radiopharmaceuticals, the biodistribution is exclusively determined by the physical properties of the metal chelate. For target-specific radiopharmaceuticals, the "metal tag" may have significant impact on the target uptake and biodistribution of the radiopharmaceutical. This is especially true for metalloradiopharmaceuticals based on small molecules since in many cases the metal chelate contributes greatly to the overall size and molecular weight. Therefore, the design and selection of the BFC is very important for the development of a new diagnostic or therapeutic radiopharmaceutical.

Metallic radionuclides, such as $^{99m}Tc$, $^{117m}Sn$, $^{111}In$, $^{67}Ga$, $^{68}Ga$, $^{89}Zr$, and $^{64}Cu$, have been proposed for diagnostic imaging. Nearly 80% of radiopharmaceuticals used in nuclear medicine are $^{99m}Tc$-labeled compounds. The reason for such a preeminent position of $^{99m}Tc$ in clinical use is its favorable physical and nuclear characteristics. The 6 h half-life is long enough to allow a radiochemist to carry out radiopharmaceutical synthesis and for nuclear medicine practitioners to collect useful images. At the same time, it is short enough to permit administration of millicurie amounts of $^{99m}Tc$ radioactivity without significant radiation dose to the patient. The monochromatic 140 KeV photons are readily collimated to give images of superior spatial resolution. Furthermore, $^{99m}Tc$ is readily available from commercial $^{99}Mo$-$^{99m}Tc$ generators at low cost.

For $^{99m}Tc$-labeling of biomolecules, bifunctional chelators include $N_2S_2$ diaminedithiols, $N_2S_2$ diaminedithiols, $N_2S_2$ monoamidemonoamidedithiols, $N_3S$ aminediamidethiols, $N_3S$ triamidethiols, and HYNIC, which forms various ternary ligand systems when used in combination with tricine/water soluble phosphines, or tricine/pyridine analogs or tricine/substituted imime-N containing heterocycles. These ternary ligand systems have been disclosed in U.S. Pat. No. 5,744,120; U.S. Pat. No. 6,010,679; U.S. Pat. No. 5,879,659; and PCT Patent Application WO 98/53858. Various $^{99m}Tc$-labeling techniques have been described in several reviews (Liu, S. and Edwards, D. S. Chem. Rev. 1999, 99, 2235–2268; Jurisson, S. and Lydon, J. D. Chem. Rev. 1999, 99, 2205–2218; Liu et al. Bioconjugate Chem. 1997, 8, 621–636). After radiolabeling, the resulting reaction mixture may optionally be purified using one or more chromatographic methods, such as Sep-Pack or high performance liquid chromatography (HPLC). The preferred radiolabeling procedures are those in which the chelation can be achieved without post-labeling purification.

Metallic radionuclides, including $^{90}Y$, $^{177}Lu$, $^{149}Pm$, $^{153}Sm$, $^{166}Ho$, $^{211}At$, $^{47}SC$, $^{109}Pd$, $^{105}Rh$, $^{186/188}Re$, and $^{67}Cu$, are potentially useful for radiotherapy. Among these radionuclides, lanthanide radioisotopes are of particular interest. There are several lanthanide isotopes to choose, including low energy β-emitter $^{177}Lu$, medium energy β-emitters, $^{149}Pm$ and $^{153}Sm$, and high-energy β-emitters, $^{166}Ho$ and 90Y. Yttrium and lanthanide metals share similar coordination chemistry. The chelator technology and their coordination chemistry are well developed and well understood.

For radionuclides, such as $^{90}$Y, $^{111}$In, $^{67}$Ga, $^{68}$Ga, $^{89}$Zr, $^{62}$Cu, $^{64}$Cu and $^{67}$Cu, diethylenetriaminepentaacetic acid (DTPA), tetraazacyclododecane-1,4,7,10-tetracetic acid (DOTA) and their derivatives would be the candidates of choice as BFCs. The macrocyclic chelators such as DOTA are known to form highly stable metal chelates due to their highly preorganized macrocyclic ligand framework. Krejcarek and Tucker (Biochem. Biophys. Res. Commun. 1976, 77, 581–588) developed an activated DTPA analog via a mixed anhydride, which can be linked to proteins. Later, Hnatowich et al (Science 1983, 220, 613–616) used the cyclic anhydride of DTPA for the same purpose. These linear BFCs bond to various metal ions and form thermodynamically stable metal chelates. However, metal chelates of linear BFCs are kinetically labile, which contributes to the loss of radionuclide from the metal chelate and often leads to severe bone marrow toxicity. Gansow et al (Bioconjugate Chem. 1991, 2, 187–194; Inorg. Chem. 1986, 25, 2772–2781) prepared a series of substituted DTPA analogs, which form metal chelates with improved solution stability.

Meares and coworkers were the first to synthesize macrocyclic BFCs (Anal. Biochem. 1985, 148, 249–253; Nucl. Med. Biol. 1986, 13, 311–318; J. Am. Chem. Soc. 1988, 110, 6266–6267), which form $^{67}$Cu and 90Y chelates with high thermodynamic stability and kinetic inertness. Macrocyclic chelants with three-dimensional cavities are of particular interest because of the high stability of the metal chelates, the substantial selectivity for certain metal ions, either by enforcing a specific spatial arrangement of donor atoms or by introducing different donor atoms into the ligand backbone, and their capability to adopt a preorganized conformation in the unchelated form. The higher the degree of preorganization of an unchelated ligand, the more stable the complex will be.

Rhenium has two isotopes, $^{186}$Re and $^{188}$Re, which might be useful in tumor therapy. $^{186}$Re has a half-life of 3.68 days with β-emission (Emax=1.07 MeV, 91% abundance) and a gamma-photon (E=137 keV, 9% abundance) which should allow imaging during therapy. Re has a half-life of 16.98 h with an intense β-emission (Emax=2.12 MeV, 85% abundance) and 155 keV gamma photons (15% abundance). The related chemistry, medical applications, and antibody labeling with $^{186/188}$Re by direct and indirect methods have recently been reviewed (Fritzberg, A. R. et al. Pharmaceutical Res. 1988, 5, 325–334; Griffiths, G. L. et al. Bioconjugate Chem. 1992, 3, 91–99; Dilworth, J. R. and Parrott, S. J. Chem. Soc. Rev. 1998, 27, 43–55). Since the rhenium chemistry is very similar to technetium chemistry due to the periodic relationship, the methods used for antibody labeling with $^{99m}$Tc should apply to that with $^{186/188}$Re.

Identifying the most appropriate isotope for radiotherapy is often a difficult task and requires weighing a variety of factors. These include tumor uptake and retention, blood clearance, rate of radiation delivery, half-life and specific activity of the radionuclide, and the feasibility of large-scale production of the radionuclide in an economical fashion. The key point for a therapeutic radiopharmaceutical is to deliver the requisite amount of radiation dose to the tumor cells and to achieve a cytotoxic or tumoricidal effect while not causing unmanageable side-effects.

The physical half-life of the therapeutic radionuclide should match the biological half-life of the target-specific radiopharmaceutical at the tumor site. If the half-life of the radionuclide is too short, much of the decay will have occurred before the radiopharmaceutical has reached maximum target/background ratio. On the other hand, too long a half-life would cause unnecessary radiation dose to normal tissues. Ideally, the radionuclide should have a long enough half-life to attain a minimum dose rate (>0.4 Gy/h) and to irradiate all the cells during the most radiation sensitive phases of the cell cycle. The half-life of a radionuclide has to be long enough to allow adequate time for manufacturing, release, and transportation of the radiopharmaceutical.

Other practical considerations in selecting a radionuclide for a given targeting biomolecule for tumor therapy include availability and quality. The purity has to be sufficient and reproducible, as trace amounts of impurities can affect the radiolabeling and the radiochemical purity of the radiopharmaceutical. The target receptor sites in tumors are typically limited in number. This requires that the chosen radionuclide have high specific activity. The specific activity depends primarily on the method of production and separation technique of the radionuclide. Trace metal contaminants must be minimized as they often compete with the radionuclide for the BFC and their metal complexes compete for receptor binding with the radiolabeled BFC-BM conjugate.

For tumor therapy, both α and β-emitters have been investigated. Alpha particles are particularly good cytotoxic agents because they dissipate a large amount of energy within one or two cell diameters. Most β-emitters are heavy elements that decay to hazardous daughter products and their penetration range is limited to only 50 μm in tissue. The short-ranged particle emitters are more attractive if the radiopharmaceutical is internalized into tumor cells. Auger electron emitters are shown to be very potent but only if they can cross the cell membrane and come into close proximity with the nucleus. This creates extra challenges for the design of new therapeutic metalloradiopharmaceuticals. The β-particle emitters have relatively long penetration range (2–12 mm in the tissue) depending upon the energy level. The long-range penetration is particularly important for solid tumors that have heterogeneous blood flow and/or receptor expression. The P-particle emitters yield a more homogeneous dose distribution even when they are heterogeneously distributed within the target tissue. Depending on the tumor size and location, the choice of the β-emitter may be different. For example, medium or low energy β-emitters such as $^{153}$Sm and $^{177}$Lu are better for smaller metastases while high-energy β-emitters such as $^{90}$Y are used for larger tumors.

The choice of radiolabeling approach depends on the type of biomolecules to be labeled and the purpose of the study. Various radiolabeling techniques for radionuclides, including $^{90}$Y, $^{111}$In, $^{67}$Ga, $^{68}$Ga, $^{89}$Zr, $^{62}$Cu, $^{64}$Cu and $^{67}$Cu, have been described in several reviews (Parker, D. Chem. Soc. Rev. 1990, 19, 271–291; Liu, F. and Wu, C. Pure & Appl. Chem. 1991, 63, 427–463; Anderson, C. J. and Welch, M. J. Chem. Rev. 1999, 99, 2219–2234; Volkert, W. A. and Hoffman, T. J. Chem. Rev. 1999, 99, 2269–2292; Liu, S and Edwards, D. S. Bioconjugate Chem. 2001, 12, 7–34).

There are two general approaches, the pre-labeling approach and the post-labeling approach, useful for the radioabeling of biomolecules with lanthanide radionuclides. In the post-labeling approach, a BFC is first attached to the biomolecule either directly or via a linker to form the BFC-BM conjugate. The radiolabeling can be accomplished simply by the reaction of the BFC-BM conjugate with the radiometal chloride in a buffer solution in the presence of weak chelating agent, if necessary. DTPA-conjugated biomolecules usually have very high radiolabeling efficiency (fast and high yield labeling), and can be readily labeled within 10 min at room temperature and pH 5–7. The high radiolabeling efficiency can be attributed to the flexibility of the linear chelator backbone of DTPA analogs. However, the radiolabeling kinetics of DOTA-conjugated biomolecules is usually slow. In this case, higher pH and elevated temperatures are often needed to achieve fast labeling and high radiolabeling yield. The post-labeling approach is useful for biomolecules that are not sensitive to the harsh radiolabeling conditions present in the chelation step. For biomolecules, which are sensitive to heating, the pre-labeling approach might be the best alternative.

The pre-labeling approach involves formation of the metal chelate with a BFC, and conjugation of the M-BFC chelate to a biomolecule in a separate step on the tracer level. In this approach, the chemistry is well defined, and the biomolecule is not exposed to the harsh conditions used in the chelation step. For research purposes, this approach is very useful to demonstrate the proof of principle in a short period of time. However, this approach is too complex and time consuming for routine clinical use. It is also not practical for large-scale production, since it involves chromatographic separations of radiolabeled molecules at high levels of radioactivity.

During radiolabeling, the pH of the reaction mixture is often controlled with a buffering agent to assure the reproducibility for the radiochemical purity of the radiopharmaceutical. The choice of a buffering agent depends upon the optimum pH value for chelation. Ammonium acetate is often used for the $^{90}$Y- or $^{111}$In-labeling of DTPA- and DOTA-conjugated biomolecules. The buffer concentration is normally 0.1–0.5 M.

A radiopharmaceutical composition including β-emitting radionuclides may undergo radiolysis during the preparation, release, transportation, and storage of the radiopharmaceutical composition. During radiolysis, emissions from the radionuclide attack other constituents of the complex or compound, or other compounds in proximity, which results in inter- and intramolecular decomposition. Radiolytic decay can result in decomposition or destruction of the radiometal chelate or the biologically active targeting molecule. Radioactivity that is not linked to the targeting biomolecule will accumulate in non-targeting tissues. Decomposition of the radiopharmaceutical composition prior to or during administration dramatically decreases the targeting potential and thus increases the toxicity of the therapeutic radiopharmaceutical composition. Thus, it is important to ensure that the radionuclide is linked to the targeting moiety and to ensure that specificity of the targeting agent is preserved.

Radiolysis is caused by the formation of free radicals such as hydroxyl and superoxide radicals (Garrison, W. M. Chem. Rev. 1987, 87, 381–398). Free radicals are very reactive towards organic molecules. The reactivity of these free radical towards organic molecules is a major factor influencing the solution stability of a therapeutic radiopharmaceutical composition. Stabilization of the therapeutic radiopharmaceutical composition is a recurrent challenge in the development of target-specific therapeutic radiopharmaceuticals. Therefore, it is very important to use a radical scavenger as a stabilizer to minimize radiolysis of the radiolabeled biomolecules.

A stabilizer is a "radical scavenging antioxidant" that readily reacts with hydroxyl and superoxide radicals. The stabilizing agent for therapeutic radiopharmaceutical composition should possess the following characteristics: low or no toxicity when it is used for human administration, no interference with the delivery or receptor binding of the radiolabeled compound to the target cells or tissue(s), and the ability to stabilize the therapeutic radiopharmaceutical for a reasonable period of time (e.g., during the preparation, release, storage and transportation of the therapeutic radiopharmaceutical).

Radical scavengers such as gentisic acid and ascorbic acid have been used to stabilize $^{99m}$Tc (DeRosch, et al, W095/33757) and $^{186/188}$Re (Anticancer Res. 1997, 17, 1783–1796) radiopharmaceuticals. U.S. Pat. No. 5,393,512 discloses the use of ascorbic acid as a stabilizing agent for $^{186}$Re and $^{131}$I-labeled antibodies or antibody fragments. Gentisic acid and gentisyl alchohol were also disclosed in U.S. Pat. No. 5,384,113 as stabilizers for radiolabeled peptides. U.S. Pat. Nos. 5,093,105 and 5,306,482 disclose the use of p-aminobenzoic acid, gentisic acid and ascorbic acid as antioxidants for $^{99m}$Tc radiopharmaceuticals. U.S. Pat. No. 5,961,955 also discloses a method of ameliorating degradation of radiolabeled peptides, especially radiolabeled proteins such as antibodies, by including PVP (polyvinylpyrrolidinone) as a radioprotectant.

A metalloradiopharmaceutical composition usually includes the BFC-BM conjugate, a buffering agent for pH control, a weak chelating agent to prevent radiometal colloid formation, and a stabilizer to prevent radiolytic degradation of the radiopharmaceutical composition during the preparation, release and transportation of the metalloradiopharmaceutical. The pH is critical for the success and reproducibility of the $^{90}$Y- or $^{111}$In-labeling of biomolecules. Controlling pH (pH 4.0–8.0) in the reaction mixture is often achieved by using 0.1–0.5 M ammonium acetate. There are two purposes in using ammonium acetate for the $^{90}$Y-labeling of biomolecules: (1) pH control during radiolabeling process and (2) ammonium acetate acts as a transfer ligand for $Y^{3+}$ by forming a weak $^{90}$Y-acetate and preventing the formation of [$^{90}$Y]colloid. The radiation stabilizer can be added into the reaction mixture before (i.e., pre-labeling addition) or after (i.e., post-labeling addition) the radiolabeling. However, the combination of a buffering agent and a stabilizer often results in high osmolarity of the radiopharmaceutical composition.

Ascorbic acid is known as an antioxidant and has been used in various pharmaceutical and radiopharmaceutical compositions. Unlike other buffering agents such as succinic acid and aminocarboxylates, ascorbic acid contains no amino or carboxylic groups. One skilled in the art would not expect to use ascorbic acid as a buffering agent and transfer ligand for the preparation of 90Y or $^{111}$In-labeled biomolecules. Therefore, it is of great significance, surprising and unexpected that ascorbic acid and its analogs can serve all three purposes: (1) as a buffering agent to control the pH of the reaction solution during radiolabeling; (2) as a transfer ligand to prevent the formation of radiometal colloid; and (3) as a stabilizer for the radiopharmaceutical composition during preparation, release, and transportation of the radiopharmaceutical composition.

SUMMARY OF THE INVENTION

There are several advantages using ascorbic acid as a buffering agent. Ascorbic acid has been approved for pharmaceutical and radiopharmaceutical applications. Ascorbic acid has a pKa of 4.2 and has the buffering capacity at pH 3.0–5.0. At higher concentrations (>50 mg/mL or 0.25 M), it may also have sufficient buffering capacity at the pH range 5.5–6.0. Since ascorbic acid contains two hydroxyl groups, one of which is deprotonable at pH>4.2, it can also be used as a transfer ligand to prevent the formation of radiometal colloids. Although the use of ascorbic acid as a stabilizer has been disclosed for a variety of diagnostic and therapeutic radiopharmaceutical compositions (see, e.g., Deausch, E. A. et al./U.S. Pat. No. 5,384,113/1995; Vanderheyden, J.-L., et al./U.S. Pat. No. 5,393,512/1995; Flanagan, R. J. and Tartaglia, D./U.S. Pat. No. 5,093,105/1992; Tartaglia, D. and Flanagan, R. J./U.S. Pat. No. 5,306,482/1994; Shochat, D. et al./U.S. Pat. No. 5,961,955/1999; and Zamora, P. O. and Merek, M. J./U.S. Pat. No. 6,066,309/2000), there is no teaching or disclosure on the use of ascorbic acid as a buffering agent and/or as a transfer ligand.

If the radiolabeling is performed in the presence of ascorbic acid at pH 4–6, there is no need for a buffering agent such as ammonium acetate in the reaction solution because ascorbic acid has sufficient buffering capacity at this pH range. In doing so, it will eliminate possible side effect from ammonium cation, a well-known vasodilator, particularly at high concentrations, and will result in dramatic reduction of the osmolarity of the radiopharmaceutical composition.

DETAILED DESCRIPTION OF THE INVENTION

One embodiment of the present invention provides a radiopharmaceutical composition comprising a radiolabeled chelator-biomolecule conjugate of the formula M-Ch-Ln-(BM)$_m$; and an amount of a compound of formula (I):

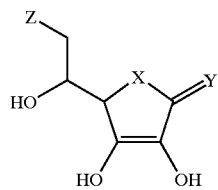

(I)

or a pharmaceutically acceptable salt thereof, wherein

X is O, NR$^1$, or CHR$^1$;

Y is O or S;

Z is hydroxyl or halogen;

R$^1$ is selected from: (C$_1$–C$_{10}$)alkyl substituted with 0–5 R$^2$, (C$_3$–C$_{10}$)cycloalkyl substituted with 0–5 R$^2$, (C$_2$–C$_{10}$)alkenyl substituted with 0–5 R$^2$, and aryl substituted with 0–5 R$^2$; and R$^2$ is independently selected at each occurrence from: NH$_2$, OH, CO$_2$H, C(=O)NH$_2$, NHC(=NH)NH$_2$, PO$_3$H$_2$, and SO$_3$H;

wherein the amount of the compound of formula (I) is effective to: (1) stabilize the radiolabeled chelator-biomolecule conjugate of the formula M-Ch-Ln-(BM)$_m$ against radiation induced degradation and to at least one of (2) control the pH of the radiopharmaceutical composition and (3) prevent radiometal colloid formation.

Another embodiment of the present invention provides a radiopharmaceutical composition of embodiment 1 wherein the amount is effective to: (1) stabilize the radiopharmaceutical against radiation induced degradation and (2) control the pH of the radiopharmaceutical.

Another embodiment of the present invention provides a radiopharmaceutical composition of embodiment [1] wherein the amount is effective to: (1) stabilize the radiopharmaceutical against radiation induced degradation and (2) prevent radiometal colloid formation.

Another embodiment of the present invention provides a radiopharmaceutical composition of embodiment [1] wherein the amount is effective to: (1) stabilize the radiopharmaceutical against radiation induced degradation, (2) control the pH of the radiopharmaceutical and (3) prevent radiometal colloid formation.

Another embodiment of the present invention provides a radiopharmaceutical composition of embodiment [1] wherein X is O.

Another embodiment of the present invention provides a radiopharmaceutical composition of embodiment [1] wherein Y is O.

Another embodiment of the present invention provides a radiopharmaceutical composition of embodiment [1] wherein Z is hydroxyl.

Another embodiment of the present invention provides a radiopharmaceutical composition of embodiment [1] wherein m is 1 to about 5.

Another embodiment of the present invention provides a radiopharmaceutical composition of embodiment [1] wherein m is 1 or 2.

Another embodiment of the present invention provides a radiopharmaceutical composition of embodiment [1] wherein m is 1.

Another embodiment of the present invention provides a radiopharmaceutical composition of embodiment [1] wherein m is 1 to about 5; X is O; and Y is O.

Another embodiment of the present invention provides a radiopharmaceutical composition of embodiment [1] wherein m is 1 or 2; X is O; Y is O; and Z is hydroxyl.

Another embodiment of the present invention provides a radiopharmaceutical composition of embodiment [1] wherein m is 1; X is O; Y is O; and Z is hydroxyl.

Another embodiment of the present invention provides a radiopharmaceutical composition of embodiment [1] wherein the concentration of the compound of formula (I) is about 2 mg/mL to about 200 mg/mL.

Another embodiment of the present invention provides a radiopharmaceutical composition of embodiment [1] wherein the metallic radioisotope is present at a level of about 10 mCi to about 2000 mCi.

Another embodiment of the present invention provides a radiopharmaceutical composition of embodiment [1] wherein the metallic radioisotope is present at a concentration of greater than about 5 mCi/mL.

Another embodiment of the present invention provides a radiopharmaceutical composition of embodiment [1] wherein the radiolabeled chelator-biomolecule conjugate of the formula M-Ch-Ln-(BM)$_m$ is a diagnostic radiopharmaceutical.

Another embodiment of the present invention provides a radiopharmaceutical composition of embodiment [1] wherein the radiolabeled chelator-biomolecule conjugate of the formula M-Ch-Ln-(BM)$_m$ is a therapeutic radiopharmaceutical.

Another embodiment of the present invention provides a radiopharmaceutical composition of embodiment [1] wherein the biomolecule is an antibody.

Another embodiment of the present invention provides a radiopharmaceutical composition of embodiment [1] wherein the biomolecule is an antibody fragment.

Another embodiment of the present invention provides a radiopharmaceutical composition of embodiment [1] wherein the biomolecule is a peptide.

Another embodiment of the present invention provides a radiopharmaceutical composition of embodiment [1] wherein the biomolecule is a peptidomimetic.

Another embodiment of the present invention provides a radiopharmaceutical composition of embodiment [1] wherein the biomolecule is a non-peptide.

Another embodiment of the present invention provides a radiopharmaceutical composition of embodiment [1] wherein the biomolecule is a cyclic IIb/IIIa receptor antagonist; an RGD containing peptide; a fibrinogen receptor antagonist; a IIb/IIIa receptor ligand; a ligand for the polymerization site of fibrin; a laminin derivative; a ligand for fibrinogen; a thrombin ligand; an oligopeptide that corresponds to the IIIa protein; a hirudin-based peptide; a IIb/IIIa receptor ligand; a thrombus, platelet binding, or atherosclerotic plaque binding peptide; a fibrin binding peptide; a hirudin-based peptide; a fibrin binding protein; a guanine derivative that binds to the IIb/IIIa receptor; a tyrosine derivative; a leukocyte binding peptide; a chemotactic peptide; a leukostimulatory agent; an LTB4 antagonist; a somatostatin analog; a selectin binding peptide; a biological-function domain; a platelet factor 4 or growth factor; a compound that binds to a receptor that is expressed or upregulated in angiogenic tumor vasculature; a peptide, polypeptide or peptidomimetic that binds with high affinity to the receptors VEGF receptors Flk-1/KDR, Flt-1, or neuropilin-1; a peptide, polypeptide or peptidomimetic that binds to $\alpha v\beta 3$, $\alpha v\beta 5$, $\alpha 5\beta 1$, $\alpha 4\beta 1$, $\alpha 1\beta 1$, or $\alpha 2\beta 2$; a compound that interacts with receptor tyrosine kinases; a protein, antibody, antibody fragment, peptide, polypeptide, or peptidomimetic that binds to receptors or binding sites on a tissue, organ, enzyme or fluid; a β-amyloid protein that has been demonstrated to accumulate in patients with Alzheimer's disease; an atrial naturetic factor derived peptide that binds to myocardial or renal receptor; an antimyosin antibody that binds to areas of infarcted tissue; or a nitroimidazole derivative that localizes in hypoxic areas in vivo.

Another embodiment of the present invention provides a radiopharmaceutical composition of embodiment [1] wherein the chelator is a cyclic or acyclic polyaminocarboxylate, a diaminedithiol, a triamidemonothiol, a monoaminemonoamidedithiol, a monoaminediamidemonothiol, a diaminedioxime, or a hydrazine.

Another embodiment of the present invention provides a radiopharmaceutical composition of embodiment [1] wherein the chelator is tetradentate, with donor atoms selected from nitrogen, oxygen and sulfur.

Another embodiment of the present invention provides a radiopharmaceutical composition of embodiment [1] wherein the chelator is diethylenetriaminepentaacetic acid (DTPA); 1,4,7,10-tetraazazcyclododecane-1,4,7,10-tetraacetic acid (DOTA); 1,4,8,11-tetraazazcyclotetradecane-1,4,8,11-tetraacetic acid (TETA); 1,4,7,10-tetraazazcyclododecane-1,4,7-triacetic acid (DO3A); 2-Benzyl-1,4,7,10-tetraazazcyclododecane-1,4,7,10-tetraacetic acid (2-Bz-DOTA); alpha-(2-phenethyl)-1,4,7,10-tetraazazcyclododecane-1-acetic-4,7,10-tris (methylacetic) acid; 2-benzyl-cyclohexyldiethylene-triaminepentaacetic acid; 2-benzyl-6-methyl-diethylenetriaminepentaacetic acid; or 6,6"-bis[N,N,N",N"-tetra(carboxymethyl)aminomethyl]-4'-(3-amino-4-methoxyphenyl)-2,2':6',2"-terpyridine.

Another embodiment of the present invention provides a radiopharmaceutical composition of embodiment [1] wherein the metallic radioisotope is $^{177}$Lu, $^{149}$Pm, $^{153}$Sm, $^{166}$Ho, $^{90}$Y, $^{111}$In, $^{67}$Ga, $^{68}$Ga, 89Zr, $^{99m}$Tc, $^{117m}$Sn, $^{203}$Pb, $^{177}$Lu, $^{47}$Sc, $^{109}$Pd, $^{105}$Rh, $^{186}$Re, $^{188}$Re, $^{60}$Cu, $^{62}$Cu, $^{64}$Cu, $^{67}$Cu, $^{97}$Ru, or $^{212}$Bi.

Another embodiment of the present invention provides a radiopharmaceutical composition of embodiment [1] wherein the metallic radioisotope is $^{99m}$Tc, $^{117m}$Sn, $^{111}$In, $^{203}$Pb, $^{67}$Ga, $^{68}$Ga, $^{89}$Zr, $^{90}$Y, $^{177}$Lu, $^{149}$Pm, 153Sm, $^{166}$Ho, $^{47}$SC, $^{109}$Pd, $^{105}$Rh, $^{186}$Re, $^{188}$Re, $^{60}$Cu, $^{62}$Cu, $^{64}$Cu or $^{67}$Cu.

Another embodiment of the present invention provides a radiopharmaceutical composition of embodiment [1] wherein the metallic radioisotope is $^{111}$In, $^{90}$Y, or $^{177}$Lu.

Another embodiment of the present invention provides a radiopharmaceutical composition comprising a radiolabeled chelator-biomolecule conjugate of the formula M-Ch-Ln-(BM)$_m$; and a compound of formula (I):

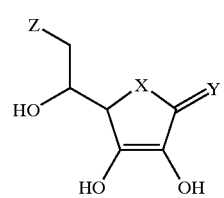

(I)

or a pharmaceutically acceptable salt thereof;
wherein
M is a metallic radioisotope;
Ch is a metal chelator;
Ln is an optional linking group;
BM is a biomolecule;
m is 1 to about 10;
X is O, NR$^1$, or CHR$^1$;
Y is O or S;
z is hydroxyl or halogen;
R$^1$ is selected from: (C$_1$–C$_{10}$)alkyl substituted with 0–5 R$^2$, (C$_3$–C$_{10}$)cycloalkyl substituted with 0–5 R$^2$, (C$_2$–C$_{10}$)alkenyl substituted with 0–5 R$^2$, and aryl substituted with 0–5 R;
R$^2$ is independently selected at each occurrence from: NH$_2$, OH, CO$_2$H, C(=O)NH$_2$, NHC(=NH)NH$_2$, PO$_3$H$_2$, and SO$_3$H;
provided the radiopharmaceutical composition does not comprise an additional buffering agent or an additional chelating agent.

Another embodiment of the present invention provides a method for buffering a radiopharmaceutical comprising contacting the radiopharmaceutical with an amount of a compound of formula (I):

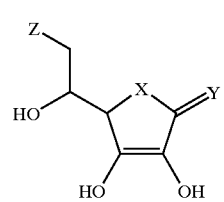

(I)

or a pharmaceutically acceptable salt thereof,
wherein
X is O, NR$^1$, or CHR$^1$;
Y is O or S;
Z is hydroxyl or halogen;
R$^1$ is selected from: (C$_1$–C$_{10}$)alkyl substituted with 0–5 R$^2$, (C$_3$–C$_{10}$)cycloalkyl substituted with 0–5 R$^2$, (C$_2$–C$_{10}$)alkenyl substituted with 0–5 R$^2$, and aryl substituted with 0–5 R;
R$^2$ is independently selected at each occurrence from: NH$_2$, OH, CO$_2$H, C(=O)NH$_2$, NHC(=NH)NH$_2$, PO$_3$H$_2$, and SO$_3$H;
wherein the amount is effective to control the pH of the radiopharmaceutical.

Another embodiment of the present invention provides a method of embodiment [32] wherein the radiopharmaceutical is a radiolabeled chelator-biomolecule conjugate of the formula M-Ch-Ln-(BM)$_m$;
wherein M is a metallic radioisotope;

Ch is a metal chelator;

Ln is an optional linking group;

BM is a biomolecule; and m is 1 to about 10.

Another embodiment of the present invention provides a method of embodiment [32] wherein the buffering agent controls the pH of the radiopharmaceutical during at least one of the preparation, release, storage, and transportation of the radiopharmaceutical.

Another embodiment of the present invention provides a method for chelating a radiopharmaceutical comprising contacting the radiopharmaceutical with an amount of a compound of formula (I):

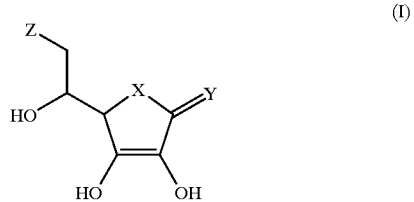

(I)

or a pharmaceutically acceptable salt thereof,
wherein

X is O, NR$^1$, or CHR$^1$;

Y is O or S;

Z is hydroxyl or halogen;

R$^1$ is selected from: (C$_1$–C$_{10}$)alkyl substituted with 0–5 R$^2$, (C$_3$–C$_{10}$)cycloalkyl substituted with 0–5 R$^2$, (C$_2$–C$_{10}$)alkenyl substituted with 0–5 R$^2$, and aryl substituted with 0–5 R;

R$^2$ is independently selected at each occurrence from: NH$_2$, OH, CO$_2$H, C(=O)NH$_2$, NHC(=NH)NH$_2$, PO$_3$H$_2$, and SO$_3$H;

wherein the amount is effective to prevent radiometal colloid formation.

Another embodiment of the present invention provides a method of embodiment [35] wherein the radiopharmaceutical is a radiolabeled chelator-biomolecule conjugate of the formula M-Ch-Ln-(BM)$_m$;
wherein M is a metallic radioisotope;

Ch is a metal chelator;

Ln is an optional linking group;

BM is a biomolecule; and m is 1 to about 10.

Another embodiment of the present invention provides a method of embodiment [35] wherein the chelating agent prevents radiometal colloid formation during at least one of the preparation, release, storage, and transportation of the radiopharmaceutical.

Another embodiment of the present invention provides a method for stabilizing a radiopharmaceutical against radiation induced degradation and at least one of (1) controlling the pH of the radiopharmaceutical and (2) preventing radiometal colloid formation; comprising contacting the radiopharmaceutical with an amount of a compound of formula (I):

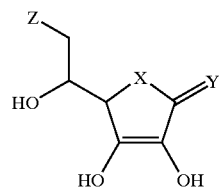

(I)

or a pharmaceutically acceptable salt thereof,
wherein x is O, NR$^1$, or CHR$^1$;

y is O or S;

Z is hydroxyl or halogen;

R$^1$ is selected from: (C$_1$–C$_{10}$)alkyl substituted with 0–5 R$^2$, (C$_3$–C$_{10}$)cycloalkyl substituted with 0–5 R$^2$, (C$_2$–C$_{10}$)alkenyl substituted with 0–5 R$^2$ and aryl substituted with 0–5 R$^2$;

R$^2$ is independently selected at each occurrence from: NH$_2$, OH, CO$_2$H, C(=O)NH$_2$, NHC(=NH)NH$_2$, PO$_3$H$_2$, and SO$_3$H;

wherein the amount is effective to: (1) stabilize the radiopharmaceutical against radiation induced degradation and to at least one of (2) control the pH of the radiopharmaceutical and (3) prevent radiometal colloid formation.

Another embodiment of the present invention provides a method of embodiment [38] wherein the amount is effective to: (1) stabilize the radiopharmaceutical against radiation induced degradation and (2) control the pH of the radiopharmaceutical.

Another embodiment of the present invention provides a method of embodiment [38] wherein the amount is effective to: (1) stabilize the radiopharmaceutical against radiation induced degradation and (2) prevent radiometal colloid formation.

Another embodiment of the present invention provides a method of embodiment [38] wherein the amount is effective to: (1) stabilize the radiopharmaceutical against radiation induced degradation, (2) control the pH of the radiopharmaceutical and (3) prevent radiometal colloid formation.

Another embodiment of the present invention provides a method of embodiment [38] wherein the radiopharmaceutical is a radiolabeled chelator-biomolecule conjugate of the formula M-Ch-Ln-(BM)$_m$
wherein M is a metallic radioisotope;

Ch is a metal chelator;

Ln is an optional linking group;

BM is a biomolecule; and m is 1 to about 10.

Another embodiment of the present invention provides a method of embodiment [38] wherein the amount is effective to: stabilize the radiopharmaceutical against radiation induced degradation and to at least one of (2) control the pH of the radiopharmaceutical and (3) prevent radiometal colloid formation; during at least one of the preparation, release, storage, and transportation of the radiopharmaceutical.

Another embodiment of the present invention provides a method for preparing a stable radiopharmaceutical composition comprising contacting a radiolabeled chelator-biomolecule conjugate of the formula M-Ch-Ln-(BM)$_m$; and an amount of a compound of formula (I):

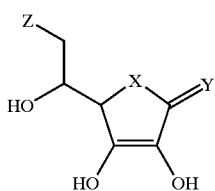

or a pharmaceutically acceptable salt thereof,
wherein

X is O, $NR^1$, or $CHR^1$;

Y is O or S;

z is hydroxyl or halogen;

$R^1$ is selected from: $(C_1-C_{10})$alkyl substituted with 0–5 $R^2$, $(C_3-C_{10})$cycloalkyl substituted with 0–5 $R^2$, $(C_2-C_{10})$alkenyl substituted with 0–5 $R^2$, and aryl substituted with 0–5 $R^2$; and $R^2$ is independently selected at each occurrence from: $NH_2$, OH, $CO_2H$, C (=O) $NH_2$, NHC (=NH) $NH_2$, $PO_3H_2$, and $SO_3H$;

wherein the amount of the compound of formula (I) is effective to: (1) stabilize the radiolabeled chelator-biomolecule conjugate of the formula M-Ch-Ln-$(BM)_m$ against radiation induced degradation and to at least one of (2) control the pH of the radiopharmaceutical composition and (3) prevent radiometal colloid formation.

Another embodiment of the present invention provides a kit comprising a sealed vial comprising a predetermined quantity of a radiolabeled chelator-biomolecule conjugate of the formula M-Ch-Ln-$(BM)_m$, and an amount of a compound of formula (I):

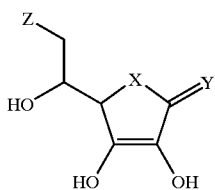

or a pharmaceutically acceptable salt thereof,
wherein

M is a metallic radioisotope;

Ch is a metal chelator;

Ln is an optional linking group;

BM is a biomolecule;

m is 1 to about 10;

X is selected from O, $NR^1$, and $CHR^1$;

Y is O or S;

Z is hydroxyl or halogen;

$R^1$ is selected from: $(C_1-C_{10})$alkyl substituted with 0–5 $R^2$, $(C_3-C_{10})$cycloalkyl substituted with 0–5 $R^2$, $(C_2-C_{10})$alkenyl substituted with 0–5 $R^2$, and aryl substituted with 0–5 R; and $R^2$ is independently selected at each occurrence from: $NH_2$, OH, $CO_2H$, C(=O) $NH_2$, NHC (=NH) $NH_2$, $PO_3H_2$, and $SO_3H$;

wherein the amount is effective to: (1) stabilize the radiolabeled chelator-biomolecule conjugate of the formula M-Ch-Ln-$(BM)_m$ against radiation induced degradation and to at least one of (2) control the pH of the radiopharmaceutical and (3) prevent radiometal colloid formation.

Another embodiment of the present invention provides a kit comprising (a) a first vial comprising a predetermined quantity of a radiolabeled chelator-biomolecule conjugate of the formula M-Ch-Ln-$(BM)_m$; and an amount of a compound of formula (I):

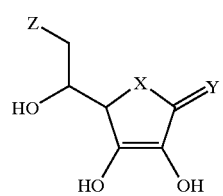

or a pharmaceutically acceptable salt thereof,
wherein

M is a metallic radioisotope;

Ch is a metal chelator;

Ln is an optional linking group;

BM is a biomolecule;

m is 1 to about 10;

X is selected from O, $NR^1$, and $CHR^1$;

Y is O or S;

Z is hydroxyl or halogen;

$R^1$ is selected from: $(C_1-C_{10})$alkyl substituted with 0–5 $R^2$, $(C_3-C_{10})$cycloalkyl substituted with 0–5 $R^2$, $(C_2-C_{10})$alkenyl substituted with 0–5 $R^2$, and aryl substituted with 0–5 $R^2$; and $R^2$ is independently selected at each occurrence from: $NH_2$, OH, $CO_2H$, C (=O) $NH_2$, NHC (=NH) $NH_2$, $PO_3H_2$, and $SO_3H$;

wherein the amount is effective to: (1) stabilize the radiopharmaceutical against radiation induced degradation and to at least one of (2) control the pH of the radiopharmaceutical and (3) prevent radiometal colloid formation; and (a) a second vial comprising a pharmaceutically acceptable carrier or diluent.

Another embodiment of the present invention provides a novel compound of formula (I):

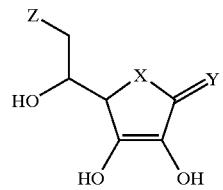

or a pharmaceutically acceptable salt thereof,
wherein

X is O, $NR^1$, or $CHR^1$;

Y is O or S;

Z is hydroxyl or halogen;

$R^1$ is selected from: $(C_1-C_{10})$alkyl substituted with 0–5 $R^2$, $(C_3-C_{10})$cycloalkyl substituted with 0–5 $R^2$, $(C_2-C_{10})$alkenyl substituted with 0–5 R and aryl substituted with 0–5 $R^2$; and $R^2$ is independently selected at each occurrence from: $NH_2$, OH, $CO_2H$, C (=O) $NH_2$, NHC (=NH) $NH_2$, $PO_3H_2$, and $SO_3H$.

It is appreciated that certain features of the invention, which are, for clarity, described in the context of separate embodiments, may also be provided in combination in a single embodiment. Conversely, various features of the invention which are for brevity, described in the context of a single embodiment, may also be provided separately or in any subcombination.

DEFINITIONS

The radiopharmaceutical compositions of the present invention are comprised of a radioisotope-chelator-biomolecule conjugate, ascorbic acid or an analog thereof, and other optional pharmaceutical excipients. The target-specific radiopharmaceuticals comprised of a gamma ray-emitting isotope or positron-emitting isotope are useful as imaging agents. The radiopharmaceuticals comprised of a beta particle, alpha particle or Auger electron-emitting isotope are useful as therapeutic radiopharmaceuticals. The metallic radioisotope is chelated by the BFC attached directly or optionally via a linker to one or more biomolecules. Biomolecules are proteins, antibodies, antibody fragments, single-chain antibodies, polypeptides, oligonucleotides, peptides, peptidomimetics or non-peptides. Preferably, the biomolecules are peptides, peptidomimetics, and non-peptides of less than 10,000 g/mol molecular weight. The ascorbic acid or analog thereof serves three purposes: it acts as a buffering agent for pH control during radiolabeling, it acts as a chelating agent to prevent radiometal colloid formation, and it acts as a stabilizer to provide protection against radiation induced degradation of the radiolabeled compound. Metallic radioisotopes that emit alpha particles, beta particles, gamma rays, positrons, or Auger electrons useful for imaging or therapy include $^{99m}Tc$, $^{117m}Sn$, $^{111}In$, $^{97}Ru$, $^{203}Pb$, $^{67}Ga$, $^{68}Ga$, $^{89}Zr$, $^{90}Y$, $^{177}Lu$, $^{149}Pm$, $^{153}Sm$, $^{166}Ho$, $^{212}Bi$, $^{47}Sc$, $^{109}Pd$, $^{105}Rh$, $^{186}Re$, $^{188}Re$, $^{60}Cu$, $^{62}Cu$, $^{64}Cu$ and $^{67}Cu$.

Examples of preferred biomolecules that may be part of the metallic radioisotope-chelator-biomolecule (M-BFC-BM) conjugate include the following.

For the diagnosis of thromboembolic disorders or atherosclerosis, BM is selected from the group including the cyclic IIb/IIIa receptor antagonist compounds described in U.S. Pat. No. 5,879,657; the RGD containing peptides described in U.S. Pat. Nos. 4,578,079, 4,792,525, the applications PCT US88/04403, PCT US89/01742, PCT US90/03788, PCT US91/02356 and by Ojima et. al. 204th Meeting of the Amer. Chem. Soc. 1992, Abstract 44; the peptides that are fibrinogen receptor antagonists described in European Patent Applications 90202015.5, 90202030.4, 90202032.2, 90202032.0, 90311148.2, 90311151.6, 90311537.6, the specific binding peptides and polypeptides described as IIb/IIIa receptor ligands, ligands for the polymerization site of fibrin, laminin derivatives, ligands for fibrinogen, or thrombin ligands in PCT WO 93/23085 (excluding the technetium binding groups); the oligopeptides that correspond to the IIIa protein described in PCT WO90/00178; the hirudin-based peptides described in PCT WO90/03391; the IIb/IIIa receptor ligands described in PCT WO90/15818; the thrombus, platelet binding or atherosclerotic plaque binding peptides described in PCT WO92/13572 (excluding the technetium binding group) or GB 9313965.7; the fibrin binding peptides described in U.S. Pat. Nos. 4,427,646 and 5,270,030; the hirudin-based peptides described in U.S. Pat. No. 5,279,812; or the fibrin binding proteins described in U.S. Pat. No. 5,217,705; the guanine derivatives that bind to the IIb/IIIa receptor described in U.S. Pat. No. 5,086,069; or the tyrosine derivatives described in European Patent Application 0478328A1, and by Hartman et. al., J. Med. Chem. 1992, 35, 4640; or oxidized low density lipoprotein (LDL).

For the diagnosis of infection, inflammation or transplant rejection, BM is selected from the group including the leukocyte binding peptides described in PCT WO93/17719 (excluding the technetium binding group), PCT WO92/13572 (excluding the technetium binding group) or U.S. Pat. No. 5,792,444; the chemotactic peptides described in Eur. Pat. Appl. 90108734.6 or A. Fischman et. Al., Semin. Nuc. Med., 1994, 24, 154: the leukostimulatory agents described in U.S. Pat. No. 5,277,892; or the LTB4 antagonists described in U.S. Pat. No. 6,416,733.

For the diagnosis of cancer, BM is selected from the group of somatostatin analogs described in UK Application 8927255.3 or PCT WO94/00489, the selectin binding peptides described in PCT WO94/05269, the biological-function domains described in PCT WO93/12819, Platelet Factor 4 or the growth factors (PDGF, VEGF, EGF, FGF, TNF MCSF or the interleukins Il1–8).

BM may also be a compound that binds a receptor that is expressed or upregulated in angiogenic tumor vasculature. For targeting the VEGF receptors, Fik-1/KDR, Fit-1, and neuropilin-1, the targeting moieties are comprised of peptides, polypeptides or peptidomimetics that bind with high affinity to the receptors. For example, peptides comprised of a 23 amino acid portion of the C-terminal domain of VEGF have been synthesized which competitively inhibit binding of VEGF to VEGFR (Soker, et al., J. Biol. Chem., 1997, 272, 31582-8). Linear peptides of 11 to 23 amino acid residues that bind to the basic FGF receptor (bFGFR) are described by Cosic et. al., Mol. and Cell. Biochem., 1994, 130, 1–9. A preferred linear peptide antagonist of the bFGFR is the 16 amino acid peptide, Met-Trp-Tyr-Arg-Pro-Asp-Leu-Asp-Glu-Arg-Lys-Gln—Gln-Lys-Arg-Glu (SEQ ID NO: 1). Gho et al. (Cancer Research, 1997, 57, 3733–40) describe the identification of small peptides that bind with high affinity to the angiogenin receptor on the surface of endothelial cells. A preferred peptide is Ala-Gln-Leu-(SEQ ID NO: 2), in which the two Cys residues form an intramolecular disulfide bond. Yayon et al. (Proc. Natl. Acad. Sci, USA, 1993, 90, 10643-7) describe other linear peptide antagonists of FGFR, identified from a random phage-displayed peptide library. Two linear 5 octapeptides, Ala-Pro-Ser-Gly-His-Tyr-Lys-Gly (SEQ ID NO: 3) and Lys-Arg-Thr-Gly-Gln-Tyr-Lys-Leu (SEQ ID NO: 4) are preferred for inhibiting binding of bFGF to it receptor.

Targeting moieties for integrins expressed in tumor vasculature include peptides, polypeptides and peptidomimetics that bind to $\alpha v\beta 3$, $\alpha v\beta 5$, $\alpha 5\beta 1$, $\alpha 4\beta 1$, $\alpha 1\beta 1$ and $\alpha 2\beta 2$. Pierschbacher and Rouslahti (J. Bid. Chem. 1987, 262, 17294–17298) describe peptides that bind selectively to $\alpha 5\beta 1$ and $\alpha v\beta 3$. U.S. Pat. No. 5,536,814 describe peptides that bind with high affinity to the integrin $\alpha 5\beta 1$. Burgess and Lim (J. Med. Chem. 1996, 39, 4520–4526) disclose the synthesis three peptides that bind with high affinity to $\alpha v\beta 3$: cyclo[Arg-Gly-Asp-Arg-Gly-Asp] (SEQ ID NO: 5), cyclo [Arg-Gly-Asp-Arg-Gly-D-Asp] (SEQ ID NO: 6) and the linear peptide Arg-Gly-Asp-Arg-Gly-Asp (SEQ ID NO: 7). U.S. Pat. No. 5,770,565 and U.S. Pat. No. 5,766,591 disclose peptides that bind with high affinity to $\alpha v\beta 3$. U.S. Pat. No. 5,767,071 and U.S. Pat. No. 5,780,426, disclose cyclic peptides that have an exocyclic Arg amino acid that have high affinity for $\alpha v\beta 3$. Srivatsa et. al., (Cardiovascular Res. 1997, 36, 408–428) describe the cyclic peptide antagonist for $\alpha v\beta 3$, cyclo [Ala-Arg-Gly-ASp-Mamb] (SEQ ID NO: 8). Tran et. al., (Bioorg. Med. Chem. Lett. 1997, 7, 997–1002) disclose the cyclic peptide cyclo[Arg-Gly-AsP- Val-Gly-Ser-BTD-Ser-Gly-Val-Ala] (SEQ ID NO: 9) that binds with high affinity to αvβ3. Arap et. al. (*Science* 1998, 279, 377–380) describe cyclicpeptides that bind to αvβ3 and αvβ5, Cys-Asp-Cys-Arg-Gl-Asp-Cys-Phe-Cys (SEQ ID NO: 10), and cyclo[Cys-Asn-Gly-Asp-Cys-] (SEQ ID NO: 11). Corbett et. al. (*Biorg. Med. Chem. Lett.* 1997, 7, 1371–1376) describe a series of αvβ3 selective peptidomimetics. And Haubner et al., (*Angew. Chem. Int. Ed. Engl.* 1997, 36, 1374–1389) disclose peptides and peptidomimetic αvβ3 antagonists obtained from peptide libraries.

Alternative targeting moieties for tumor vasculature include compounds that interact with receptor tyrosine kinases. Receptor tyrosine kinases (TKs) are membrane proteins, which play a key role in the transduction of mitogenic signals across the cell to the nucleus (Rewcastle, G. W. et al *J. Med. Chem.* 1995, 38, 3482–3487; Thompson, A. M. et al *J. Med. Chem.* 1997, 40, 3915–3925). Of the many TKs that have been identified and characterized, those of the epidermal growth factor receptor (EGFR) family are particularly important, and have been implicated in a variety of ectopic cell proliferative processes. The over-expression of human EGF receptor is greatly amplified in several human tumors (Fry, D. W. *Exp. Opin. Invest. Drugs* 1994, 3, 577–595; Jardines, L. et al *Pathobiology* 1993, 61, 268–282), accompanied by an overphosphorylation of their protein targets. This increased phosphorylation of substrate tyrosine residues by oncogenic TK proteins is an essential step in the neoplastic transformation. Consequently, there has been great interest in developing inhibitors of TKs (TKIs) as anticancer drugs (Burke, T. R. Jr. *Drugs Future* 1992 17, 119–131; Chang, C. J. and Geahlen, R. J. Nat. Prod. 1992, 55, 1529–1560). The over-expression of EGF receptors in tumor cells also provides the foundation for the development of diagnostic and therapeutic radiopharmaceuticals by attaching a chelator and a radionuclide onto the TK receptor ligand (tyrosine kinase inhibitor).

BM may also represent proteins, antibodies, antibody fragments, peptides, polypeptides, or peptidomimetics that bind to receptors or binding sites on other tissues, organs, enzymes or fluids. Examples include the β-amyloid proteins that have been demonstrated to accumulate in patients with Alzheimer's disease, atrial naturetic factor derived peptides that bind to myocardial and renal receptors, antimyosin antibodies that bind to areas of infarcted tissues, or nitroimidazole derivatives that localize in hypoxic areas in vivo.

The linking group Ln can serve several roles. First it provides a spacing group between the metal chelator, Ch, and the one or more of the biomolecules, BM, so as to minimize the possibility that the metal chelate M-Ch will interfere with the interaction of the biomolecule with its biological target. The necessity of incorporating a linking group in a reagent is dependent on the identity of BM and M-Ch. If metal chelate M-Ch cannot be attached to BM without substantially diminishing its affinity for its biological target, then a linking group is used. A linking group also provides a means of independently attaching multiple biomolecules to one group that is attached to M-Ch.

The linking group also provides a way of incorporating a pharmacokinetic modifier into the pharmaceuticals of the present invention. The pharmacokinetic modifier serves to direct the biodistribution of the injected pharmaceutical other than by the interaction of the biomolecules, BM, with the biological target. A wide variety of functional groups can serve as pharmacokinetic modifiers, including, but not limited to, carbohydrates, polyalkylene glycols, peptides or other polyamino acids, and cyclodextrins. The modifiers can be used to enhance or decrease hydrophilicity and to enhance or decrease the rate of blood clearance. The modifiers can also be used to direct the route of elimination of the pharmaceuticals.

The metal chelator or bonding moiety, Ch, is selected to form stable complexes with the metal ion chosen for the particular application. Chelators or bonding moieties for diagnostic radiopharmaceuticals are selected to form stable chelates with the radioisotopes that have imageable gamma ray or positron emissions.

Chelators for technetium and rhenium isotopes are selected from diaminedithiols, triamidemonothiols, monoaminemonoamidedithiols, monoaminediamide-monothiols, diaminedioximes, and hydrazines. The chelators are generally tetradentate with donor atoms selected from nitrogen, oxygen and sulfur. Preferred reagents are comprised of chelators having amine nitrogen and thiol sulfur donor atoms and hydrazine bonding units. The thiol sulfur atoms and the hydrazines may bear a protecting group which can be displaced either prior to using the reagent to synthesize a radiopharmaceutical or preferably in situ during the synthesis of the radiopharmaceutical.

Exemplary thiol protecting groups include those listed in Greene and Wuts, "Protective Groups in Organic Synthesis" John Wiley & Sons, New York (1991), the disclosure of which is hereby incorporated by reference. Any thiol protecting group known in the art can be used. Examples of thiol protecting groups include, but are not limited to, the following: acetamidomethyl, benzamidomethyl, 1-ethoxyethyl, benzoyl, and triphenylmethyl.

Exemplary protecting groups for hydrazine bonding units are hydrazones which can be aldehyde or ketone hydrazones having substituents selected from hydrogen, alkyl, aryl and heterocycle. Particularly preferred hydrazones are described in U.S. Pat. No. 5,750,088, the disclosure of which is herein incorporated by reference in its entirety.

The hydrazine-bonding unit when bound to a metal radionuclide is termed a hydrazido, or diazenido group and serves as the point of attachment of the radionuclide to the remainder of the radiopharmaceutical. A diazenido group can be either terminal (only one atom of the group is bound to the radionuclide) or chelating. In order to have a chelating diazenido group at least one other atom of the group must also be bound to the radionuclide. The atoms bound to the metal are termed donor atoms.

Chelators for chelation of radioniclides, including $^{111}$In, $^{86}$Y, $^{67}$Ga, $^{68}$Ga, $^{89}$Zr, $^{62}$Cu, $^{64}$Cu and $^{67}$Cu, are selected from polyaminocarboxylates, such as diethylenetriaminepentaacetic acid (DTPA), 1,4,7,10-tetraazazcyclododecane-1,4,7,10-tetraacetic acid (DOTA), 1,4,8,11-tetraazazcyclotetradecane-1,4,8,11-tetraacetic acid (TETA), 1,4,7,10-tetraazazcyclododecane-1,4,7-triacetic acid (DO3A), 2-Benzyl-1,4,7,10-tetraazazcyclododecane-1,4,7,10-tetraacetic acid (2-Bz-DOTA), alpha-(2-phenethyl)-1,4,7,10-tetraazazcyclododecane-1-acetic-4,7,10-tris (methylacetic) acid, 2-benzyl-cyclohexyldiethylenetriaminepentaacetic acid, 2-benzyl-6-methyl-diethylenetriaminepentaacetic acid, and 6,6"-bis[N,N,N",N"-tetra(carboxymethyl)aminomethyl)-4'-(3-amino-4-methoxyphenyl)-2,2':6',2"-terpyridine. Procedures for synthesizing these chelators that are not commercially available can be found in Brechbiel, M. and Gansow, O., J. Chem. Soc. Perkin Trans. 1992, 1, 1175; Brechbiel, M. and Gansow, O., Bioconjugate Chem. 1991, 2, 187; Deshpande, S., et. al., J. Nucl. Med. 1990, 31, 473; Kruper, J., U.S. Pat. No. 5,064,956, and Toner, J., U.S. Pat. No. 4,859,777, the disclosures of which are hereby incorporated by reference in their entirety.

Chelators or bonding moieties for therapeutic radiopharmaceuticals are selected to form stable complexes with the radioisotopes that have alpha particle, beta particle, Auger or Coster-Kronig electron emissions. Chelators for rhenium, copper, palladium, platinum, iridium, rhodium, silver and gold isotopes are selected from diaminedithiols, monoaminemonoamidedithiols, triamidemonothiols, monoaminediamidemonothiols, diaminedioximes, and hydrazines. Chelators for yttrium, bismuth, and the lanthanide isotopes are selected from cyclic and acyclic polyaminocarboxylates, including diethylenetriaminepentaacetic acid (DTPA), 1,4,7,10-tetraazazcyclododecane-1,4,7,10-tetraacetic acid (DOTA), 1,4,8,11-tetraazazcyclotetradecane-1,4,8,11-tetraacetic acid (TETA), 1,4,7,10-tetraazazcyclododecane-1,4,7-triacetic acid (DO3A), 2-Benzyl-1,4,7,10-tetraazazcyclododecane-1,4,7,10-tetraacetic acid (2-Bz-DOTA), alpha-(2-phenethyl)-1,4,7,10-tetraazazcyclododecane-1-acetic-4,7,10-tris(methylacetic) acid, 2-benzyl-cyclohexyldiethylenetriaminepentaacetic acid, 2-benzyl-6-methyl-diethylenetriaminepentaacetic acid, and 6,6"-bis[N,N,N",N"'-tetra(carboxymethyl)aminomethyl)-4'-(3-amino-4-methoxyphenyl)-2,2':6', 2"-terpyridine.

The integrity of a radiopharmaceutical is measured by the radiochemical purity (RCP) of the radiolabeled compound using ITLC or more preferably HPLC. The advantage of using HPLC is that radio-impurities caused by radiolytic degradation can be separated from the radiopharmaceutical under optimized chromatographic conditions. Improved stability over time for radiopharmaceutical compositions of this invention can be demonstrated by determining the change in RCP of the radiolabeled compound in samples taken at representative time points. The radiopharmaceutical compositions of this invention are effective in maintaining the long-term stability of samples that have been frozen, thawed, and re-tested up to 5 days post-labeling.

The initial RCP of a radiopharmaceutical is largely dependent on radiolabeling conditions such as pH, heating temperature and time. Once a radiopharmaceutical is prepared in high yield, the ability of an antioxidant to stabilize a radiopharmaceutical composition is measured by the RCP change over a certain period of time.

Therapeutic radiopharmaceutical compositions are preferably stored at low temperature to avoid extensive radiolysis during release and transportation. The amount of the stabilizer used in the therapeutic radiopharmaceutical composition and storage temperature during release and transportation may be adjusted according to the sensitivity of a specific radiolabeled compound towards radiolytic decomposition.

Ascorbic acid is known as vitamin C, and is a commonly used antioxidant to prevent radiolytic decomposition of $^{99m}$Tc and $^{186/188}$Re radiopharmaceuticals (WO95/33757; Anticancer Res. 1997, 17, 1783–1796; U.S. Pat. No. 5,093,105, and U.S. Pat. No. 5,306,482) or radiolabeled peptides (U.S. Pat. No. 5,393,512; U.S. Pat. No. 5,384,113 and U.S. Pat. No. 5,961,955). Ascorbic acid is readily available GRAS (generally recognized as safe) substance often used in pharmaceutical compositions and other formulations used for biological purpose and may be used at levels as high as 200 mg/mL of the final formulation. The major advantages of using ascorbic acid or its analogs in a radiopharmaceutical composition disclosed in this invention include: (1) the radiopharmaceutical can be prepared in high yield (>90%); (2) the radiometal colloid formation is minimal (<1%); and (3) the radiopharmaceutical composition can be stored for several days, while maintaining the RCP (>90%) of the radiopharmaceutical.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., ═O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^5$) occurs more than one time in any constituent or formula for a compound, its definition at each occurrence is independent of its definition at every other occurrence. Thus, for example, if a group is shown to be substituted with 0–2 $R^5$, then said group may optionally be substituted with up to two $R^5$ groups and $R^5$ at each occurrence is selected independently from the definition of $R^9$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Cycloalkyl" is intended to include saturated ring groups, such as cyclopropyl, cyclobutyl, or cyclopentyl. "Alkenyl" is intended to include hydrocarbon chains of either a straight or branched configuration and one or more unsaturated carbon—carbon bonds which may occur in any stable point along the chain, such as ethenyl and propenyl. "Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3- to 7-membered monocyclic or bicyclic or 7-to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5-to 7-membered monocyclic or bicyclic or 7-to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5-to 7-membered monocyclic or bicyclic or 7-to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The term "amino acid' as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) The Peptides, 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl) cyclohexanecarboxylic acid, 2-, 3-, and 4-(aminomethyl) benzoic acid, 1-aminocyclopentanecarboxylic acid, 1-aminocyclopropanecarboxylic acid, and 2-benzyl-5-aminopentanoic acid.

The term "peptide" as used herein means a linear compound that consists of two or more amino acids (as defined herein) that are linked by means of a peptide bond. A "peptide" as used in the presently claimed invention is intended to refer to a moiety with a molecular weight of less than 10,000 Daltons, preferable less than 5,000 Daltons, and more preferably less than 2,500 Daltons. The term "peptide" also includes compounds containing both peptide and non-peptide components, such as pseudopeptide or peptidomimetic residues or other non-amino acid components. Such a compound containing both peptide and non-peptide components may also be referred to as a "peptide analog".

A "pseudopeptide" or "peptidomimetic" is a compound which mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue. A "pseudopeptide residue" means that portion of an pseudopeptide or peptidomimetic that is present in a peptide.

The term "peptide bond" means a covalent amide linkage formed by loss of a molecule of water between the carboxyl group of one amino acid and the amino group of a second amino acid.

The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

The term "non-peptide" refers to a compound in comprised of preferably less than three amide bonds in the backbone core compound or preferably less than three amino acids or amino acid mimetics.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Penn., 1985, p. 1418, the disclosure of which is hereby incorporated by reference.

"Stable compound" and "stable structure" are meant to indicate a compound that is sufficiently robust to survive isolation to a useful degree of purity from a reaction mixture, and formulation into an efficacious therapeutic agent.

Lyophilization aids useful in the preparation of diagnostic kits useful for the preparation of radiopharmaceuticals include but are not limited to mannitol, lactose, sorbitol, dextran, Ficoll, and polyvinylpyrrolidine (PVP).

Solubilization aids useful in the preparation of radiopharmaceuticals and in diagnostic kits useful for the preparation of said radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly(oxyethylene) block copolymers (Pluronics) and lecithin. Preferred solubilizing aids are polyethylene glycol, and Pluronics.

Bacteriostats useful in the preparation of radiopharmaceuticals and in diagnostic kits useful for the preparation of said radiopharmaceuticals include but are not limited to benzyl alcohol, benzalkonium chloride, chlorbutanol, and methyl, propyl or butyl paraben.

EXPERIMENTAL

The integrity of a radiopharmaceutical is measured by the radiochemical purity (RCP) of the radiolabeled compound using ITLC or more preferably HPLC. The advantage of using HPLC is that radio-impurities caused by radiolytic degradation can be separated from the radiopharmaceutical under optimized chromatographic conditions. Improved stability over time for radiopharmaceutical compositions of this invention can be demonstrated by determining the change in RCP of the radiolabeled compound in samples taken at representative time points. The radiopharmaceutical compositions of this invention are effective in maintaining the long-term stability of samples that have been frozen, thawed, and re-tested periodically for 5 days.

The initial RCP of a radiopharmaceutical is largely dependent on radiolabeling conditions such as pH, heating temperature and time. Once a radiopharmaceutical is prepared in high yield, the stability of the radiopharmaceutical composition is measured by the RCP change of the radiopharmaceutical over a certain period of time.

Materials. Acetic acid (ultra-pure), ammonium hydroxide (ultra-pure), ascorbic acid (sodium salt), and sodium gentisate were purchased from either Aldrich or Sigma Chemical Co., and were used as received. $^{90}YCl_3$ and $^{111}In\ Cl_3$ (in 0.05 N HCl) were purchased from NEN®, N. Billerica, Mass. High specific activity $^{177}LuCl_3$ was obtained from University of Missouri Research Reactor, Columbia, Mo.

Analytical Methods. HPLC method 1 used a HP-1100 HPLC system with a UV/visible detector ($\Delta$=220 nm), an IN-US radio-detector, and a Zorbax $C_{18}$ column (4.6 mm×250 mm, 80 A pore size). The flow rate was 1 mL/min with the mobile phase starting with 92% solvent A (0.025 M ammonium acetate buffer, pH 6.8) and 8% solvent B (acetonitrile) to 90% solvent A and 8% solvent B at 18 min, followed by an isocratic wash using 40% of solvent A and 60% solvent B from 19 to 25 min.

HPLC method 2 used a HP-1100 HPLC system with a UV/visible detector ($\Delta$=220 nm), an IN-US radio-detector, and a Zorbax $C_{18}$ column (4.6 mm×250 mm, 80 A pore size). The flow rate was 1 mL/min with the mobile phase starting with 92% solvent A (0.025 M ammonium acetate buffer, pH 6.8) and 8% solvent B (acetonitrile) to 80% solvent A and 20% solvent B at 18 min, followed by an isocratic wash using 40% of solvent A and 60% solvent B from 19 to 25 min.

HPLC method 3 used a HP-1100 HPLC system with a UV/visible detector (k=220 nm), an IN-US radio-detector, and a Zorbax $C_{18}$ column (4.6 mm×250 mm, 80 A pore size). The flow rate was 1 mL/min with an isocratic mobile phase with 92% solvent A (0.025 M ammonium acetate buffer, pH 6.8) and 8% solvent B (acetonitrile) over 25 min, followed by an isocratic wash using 40% of solvent A and 60% solvent B from 26 to 30 min.

The ITLC method used reverse phase $C_{18}$ TLC plates and a mixture of methanol, acetone and saline (2:1:1=v:v:v) as eluant. By this method, the radiolabeled compounds migrate to the solvent front while [$^{90}Y$/$^{177}Lu$]colloid and [$^{90}Y$]/$^{177}Lu$]acetate remain at the origin.

EXAMPLE 1

Preparation $^{90}$Y-(2S)-2-[({2,6-Dimethyl-4-[3-(N-{2-[3-sulfo-2-(3-sulfo-2-{2-[1,4,7,10-tetraaza-4,7,10-tris (carboxymethyl) cyclododecyl]acetylamino}propyl)-propyl]ethyl}carbamoyl)propoxy]phenyl}sulfonyl)amino]-3-({7-[(imidazol-2-ylamino)methyl]-1-methyl-4-oxo(3-hydroquinolyl)}carbonylamino)propanoic Acid Trifluoroacetate Salt (20 mCi) Using Ascorbic Acid (AA, 0.1 M or 20 mg/mL, pH=7.35) as a buffer agent, Transfer Ligand and Radiolytic Stabilizer.

(2S)-2-[({2,6-Dimethyl-4-[3-(N-{2-[3-sulfo-2-(3-sulfo-2-{2-[1,4,7,10-tetraaza-4,7,10-tris(carboxymethyl) cyclododecyl]acetylamino}propyl)propyl]ethyl}-carbamoyl)-propoxy]phenyl}sulfonyl)amino]-3-({7-[(imidazol-2-ylamino)methyl]-1-methyl-4-oxo(3-hydroquinolyl)}-carbonylamino)propanoic acid trifluoroacetate salt was prepared as disclosed in U.S. patent application Ser. No. 09/456,300 and was subsequently dissolved in 0.1 M ascorbic acid buffer (pH 7.35) to give a concentration of 100 $\mu$g/mL. The resulting solution was immediately degassed under vacuum for another 1–2 min. To a clean sealed 5 mL vial was added 1.0 mL of 0.1 M ascorbic acid (sodium salt) buffer (pH 7.35) containing 100 $\mu$g of (2S)-2-[({2,6-Dimethyl-4-[3-(N-{2-[3-sulfo-2-(3-sulfo-2-{2-[1,4,7,10-tetraaza-4,7,10-tris(carboxymethyl) cyclododecyl]acetylamino}propyl)propyl]ethyl}carbamoyl)-propoxy]phenyl}sulfonyl)amino]-3-({7-[(imidazol-2-ylamino)methyl]-1-methyl-4-oxo(3-hydroquinolyl)}-carbonylamino)propanoic acid trifluoroacetate. The solution was degassed again under vacuum. Upon addition of ~10 $\mu$L of $^{90}$YCl$_3$ solution (20.5 mCi) in 0.05 N HCl, the reaction mixture was heated at 95° C. for 5 min. After cooling to room temperature, a sample of the resulting solution was diluted 50-fold with saline containing sodium gentisate (10 mg/mL), and was then analyzed by HPLC (Method 1, injection volume=5 $\mu$L). The RCP was 99.3%. The retention time was 14.7 min. The TLC (reverse phase C$_{18}$ TLC) showed minimal (0.38%) [$^{90}$Y] colloid and [$^{90}$Y]acetate impurities.

This clearly shows that $^{90}$Y-(2S)-2-[({2,6-Dimethyl-4-[3-(N-{2-[3-sulfo-2-(3-sulfo-2-{2-[1,4,7,10-tetraaza-4,7,10-tris(carboxymethyl) cyclododecyl]acetylamino}propyl)--propyl]ethyl}carbamoyl)propoxy]phenyl}sulfonyl)amino]-3-({7-[(imidazol-2-ylamino)methyl]-1-methyl-4-oxo(3-hydroquinolyl)}carbonylamino)propanoic acid trifluoroacetate can be prepared in high yield and radiochemical purity using ascorbic acid as a buffer agent for pH control and a weak transfer ligand to prevent the formation of [$^{90}$Y]colloid. Based on the results, a radiolabeling experiment was designed to find optimal radiolabeling conditions in using ascorbic acid as a buffering agent for pH control, a transfer ligand to prevent [$^{90}$Y]colloid formation, and as a stabilizer for the solution stability of $^{90}$Y-(2S)-2-[({2,6-Dimethyl-4-[3-(N-{2-[3-sulfo-2-(3-sulfo-2-{2-[1,4,7,10-tetraaza-4,7,10-tris(carboxymethyl) cyclododecyl] acetylamino}propyl)propyl]ethyl}carbamoyl)-propoxy] phenyl}sulfonyl)amino]-3-({7-[(imidazol-2-ylamino) methyl]-1-methyl-4-oxo(3-hydroquinolyl)}-carbonylamino)propanoic acid trifluoroacetate. Four factors were considered in the experimental design. These include pH value (5, 6, and 7), heating time (5 min and 35 min), sodium ascorbic level (20 mg and 100 mg), and temperature (50° C. and 95° C.). Each condition contains two vials. The activity level for each vial was ~10 mCi. The reaction mixture from each vial was characterized by HPLC and reverse phase C$_{18}$ TLC.

Based on the radiolabeling results, it is clear that (1) AA level does not have a significant effect on the RCP as long as the heating temperature is 95° C.; (2) the pH shows little effect on the RCP at pH=5–7; (3) a longer heating time gives slightly better RCP at 95° C.; and (4) heating temperature is the most dominant factor on RCP.

EXAMPLE 2

Preparation and Solution Stability of $^{90}$Y-(2S)-2-[({2,6-Dimethyl-4-[3-(N-{2-[3-sulfo-2-(3-sulfo-$^{2}$-{$^{2}$-[1,4,7,10-tetraaza-4,7,10-tris(carboxymethyl) cyclododecyl] acetylamino}--propyl)propyl]ethyl}carbamoyl)-propoxy] phenyl}sulfonyl)amino]-$^{3}$-({$^{7}$-[(imidazol-2-ylamino) methyl]-1-methyl-4-oxo(3-hydroquinolyl)}-carbonylamino)propanoic acid trifluoroacetate (100 mCi Level) Using Ascorbic Acid (AA, 20 mg/mL or 0.1 M, pH=5.0) as the buffer agent, Transfer Ligand and Radiolytic Stabilizer.

(2S)-2-[({2,6-Dimethyl-4-[3-(N-{2-[3-sulfo-2-(3-sulfo-2-{2-[1,4,7,10-tetraaza-4,7,10-tris(carboxymethyl) cyclododecyl]acetylamino}propyl)propyl] ethyl}carbamoyl)-propoxy]phenyl}sulfonyl)amino]-3-({7-[(imidazol-2-ylamino)methyl]-1-methyl-4-oxo(3-hydroquinolyl)}-carbonylamino)propanoic acid trifluoroacetate was prepared as disclosed in U.S. patent application Ser. No. 09/456,300 and was subsequently dissolved in 0.1 M AA buffer (pH 5.0) to give a concentration of 100 $\mu$g/mL. The resulting solution was immediately degassed under vacuum for another 1–2 min. To a clean sealed 5 mL vial was added 5.0 mL of 0.1 M ascorbic acid buffer (pH 5.0) containing 500 $\mu$g of (2S)-2-[({2,6-Dimethyl-4-[3-(N-{2-[3-sulfo-2-(3-sulfo-2-{2-[1,4,7,10-tetraaza-4,7,10-tris(carboxymethyl) cyclododecyl] acetylamino}propyl) propyl]ethyl}carbamoyl)propoxy] phenyl}sulfonyl)amino]-3-({7-[(imidazol-2-ylamino) methyl]-1-methyl-4-oxo(3-hydroquinolyl)}carbonylamino) propanoic acid trifluoroacetate. The solution was degassed again under vacuum. Upon addition of ~75 $\mu$L of $^{90}$YCl$_3$ solution (101.5 mCi) in 0.05 N HCl, the reaction mixture was heated at 95° C. for 30 min. After cooling to room temperature, a sample of the resulting solution was diluted 50-fold with saline containing sodium gentisate (10 mg/mL), and was then analyzed by HPLC (Method 1, injection volume 5 $\mu$L). The resulting mixture was then kept in a dry-ice box (–78° C.) for 5 days. Samples were analyzed at t=0 (RCP=98.5%), 24 h (RCP=98.4%), 68 h (RCP=98.0%), and 120 h (RCP=98.8%). The retention time was 14.8 min.

This experiment clearly demonstrated that $^{90}$Y-(2S)-2-[({2,6-Dimethyl-4-[3-(N-{2-[3-sulfo-2-(3-sulfo-2-{2-[1,4,7,10-tetraaza-4,7,10-tris(carboxymethyl) cyclododecyl] acetylamino}--propyl)propyl]ethyl}carbamoyl)-propoxy] phenyl}sulfonyl)amino]-3-({7-[(imidazol-2-ylamino) methyl]-1-methyl-4-oxo(3-hydroquinolyl)}-carbonylamino)propanoic acid trifluoroacetate can be readily prepared in high RCP (>98%) under the following conditions: 500 $\mu$g (2S)-2-[({2,6-Dimethyl-4-[3-(N-{2-[3-sulfo-2-(3-sulfo-2-{2-[1,4,7,10-tetraaza-4,7,10-tris (carboxymethyl) cyclododecyl]acetylamino}propyl)propyl] ethyl}carbamoyl)-propoxy]phenyl}sulfonyl)amino]-3-({7-[(imidazol-2-ylamino)methyl]-1-methyl-4-oxo(3-hydroquinolyl)}-carbonylamino)propanoic acid trifluoroacetate for 100 mCi of $^{90}$Y in 5 mL of AA solution containing 100 mg AA, pH=5.0, heating at 95° C. for 30 min and remains stable for at least 5 days (RCP>96%). Ascorbic acid can be used as a buffer agent, a transfer ligand, and a radiolytic stabilizer for the routine preparation and stabilization of $^{90}$Y-labeled biomolecules.

EXAMPLE 3

Preparation and Solution Stability of $^{111}$In-(2S)-2-[({2,6-Dimethyl-4-[3-(N-{2-[3-sulfo-2-(3-sulfo-2-{2-[1,4,7,10- tetraaza-4,7,10-tris(carboxymethyl) cyclododecyl]acetylamino}--propyl)propyl]ethyl}carbamoyl)-propoxy]phenyl}sulfonyl)amino]-3-({7-[(imidazol-2-ylamino)methyl]-1-methyl-4-oxo(3-hydroquinolyl)}-carbonylamino)propanoic acid trifluoroacetate (2.8 mCi) Using Ascorbic Acid (AA, 20 mg/mL or 0.1 M) as the Buffer agent, Transfer Ligand, and Radiolytic Stabilizer.

(2S)-2-[({2,6-Dimethyl-4-[3-(N-{2-[3-sulfo-2-(3-sulfo-2-{2-[1,4,7,10-tetraaza-4,7,10-tris(carboxymethyl) cyclododecyl]acetylamino}propyl)propyl]ethyl}carbamoyl)-propoxy]phenyl}sulfonyl)amino]-3-({7-[(imidazol-2-ylamino)methyl]-1-methyl-4-oxo(3-hydroquinolyl)}-carbonylamino)propanoic acid trifluoroacetate was prepared as disclosed in U.S. patent application Ser. No. 09/456,300 and was subsequently dissolved in 0.1 M ascorbic acid buffer (pH 6.0) to give a concentration of 100 μg/mL. The resulting solution was immediately degassed under vacuum for another 1–2 min. To a clean sealed 5 mL vial was added 2.0 mL of 0.1 M ascorbic acid buffer (pH 6.0) containing 150 μg of (2S)-2-[({2,6-Dimethyl-4-[3-(N-{2-[3-sulfo-2-(3-sulfo-2-{2-[1,4,7,10-tetraaza-4,7,10-tris(carboxymethyl) cyclododecyl]acetylamino}propyl)propyl]ethyl}carbamoyl)-propoxy]phenyl}sulfonyl)amino]-3-({7-[(imidazol-2-ylamino)methyl]-1-methyl-4-oxo(3-hydroquinolyl)}-carbonylamino)propanoic acid trifluoroacetate. The solution was degassed again under vacuum. Upon addition of ~7 μL of $^{111}$InCl$_3$ solution (2.8 mCi) in 0.05 N HCl, the reaction mixture was heated at 100° C. for 5 min. After cooling to room temperature, a sample of the resulting solution was then analyzed by HPLC (Method 3, injection volume=10 μL). The resulting mixture was then kept at room temperature for 24 hours. Samples were analyzed at t 0 (RCP 98.2%) and 24 h (RCP=97.6%). The retention time was 11.7 min. This clearly demonstrated that $^{111}$In-(2S)-2-[({2,6-Dimethyl-4-[3-(N-{2-[3-sulfo-2-(3-sulfo-2-{2-[1,4,7,10-tetraaza-4,7,10-tris(carboxymethyl) cyclododecyl]acetylamino}propyl)propyl]ethyl}carbamoyl)-propoxy]phenyl}sulfonyl)amino]-3-({7-[(imidazol-2-ylamino)methyl]-1-methyl-4-oxo(3-hydroquinolyl)}-carbonylamino)propanoic acid trifluoroacetate could be prepared in high yield using ascorbic acid as a buffer agent, a transfer ligand and a radiolytic stabilizer. $^{111}$In-(2S)-2-[({2,6-Dimethyl-4-[3-(N-{2-[3-sulfo-2-(3-sulfo-2-{2-[1,4,7,10-tetraaza-4,7,10-tris(carboxymethyl) cyclododecyl]acetylamino}propyl)propyl]ethyl}carbamoyl)-propoxy]phenyl}sulfonyl)amino]-3-({7-[(imidazol-2-ylamino)methyl]-1-methyl-4-oxo(3-hydroquinolyl)}-carbonylamino)propanoic acid trifluoroacetate remains stable in solution for at least 24 hours. Ascorbic acid can be used as a buffer agent, a transfer ligand, and a radiolytic stabilizer for the routine preparation and stabilization of $^{111}$In-labeled biomolecules.

EXAMPLE 4

Preparation and Solution Stability of $^{177}$Lu-DOTA/(2S)-2-{[(4-{3-[N-(2-{2-[(4S)-4-(N-{1-[N-(2-{4-[4-({[(1S)-1-Carboxy-2-({7-[(imidazol-2-ylamino)methyl]-1-methyl-4-oxo(3-hydroquinolyl)}-carbonylamino)ethyl]amino}sulfonyl)-3,5-dimethylphenoxy]butanoylamino}ethyl)carbamoyl]-2-sulfoethyl}carbamoyl)-4-aminobutanoylamino]-dimethylphenyl)sulfonyl]amino}-3-({7-[(imidazol-2-ylamino)methyl]-1-methyl-4-oxo(3-hydroquinolyl)}-carbonylamino)propanoic Acid Conjugate Bis(trifluoroacetate) Using Ascorbic Acid (AA, 20 mg/mL or 0.1 M) as the buffer agent, Transfer Ligand and Radiolytic Stabilizer.

To a clean sealed 5 mL vial was added 2.0 mL of 0.1 M ascorbic acid buffer (pH 6.0) containing 137 μg of DOTAl (2S)-2-{[4-{3-[N-(2-{2-{(4S)-4-(N-{1 -[N-(2-{4-[4-({[(1S)-1-Carboxy-2-({7-[(imidazol-2-ylamino)methyl]-1-methyl-4-oxo(3-hydroquinolyl)}-carbonyl amino)ethyl]amino}ethyl)carbamoyl]-2-sulfoethyl}carbamoyl)-40amino butanoylamino]-3-sulfopropyl}ethyl)carbamoyl]propoxy}-2,6-dimethylphenyl)sulfonyl]amino}-3-({7-[(imidazol-2-ylamino)methyl]-1-methyl-4-oxo(3-hydroquinolyl)}-carbonylamino)propanoic Acid Conjugate Bis (trifluroacetate) which was prepared as disclosed in US Publication No. US20020182147A1. The solution was degassed again under vacuum. Upon addition of ~6 μL of $^{177}$LuCl$_3$ solution (~17 mCi) in 0.05 N HCl, the reaction mixture was heated to 95° C. for 45 mm. After cooling to room temperature, a sample of the resulting solution was analyzed by HPLC (Method 2, injection volume=2 μL) and reverse phase C$_{18}$ TLC. The radiochemical purity was 94.9% at 0 h and 95% at 24 h post-labeling. The TLC showed minimal [$^{177}$Lu]colloid and [$^{177}$Lu]acetate impurities at the origin (~1.2% by TLC).

It is clear that $^{177}$Lu-DOTA/(2S)-2-{[(4-{3-[N-(2-{2-[(4S)-4-(N-{1-[N-(2-{4-[4-({[(1S)-1-Carboxy-2-({7-[(imidazol-2-ylamino)methyl]-1-methyl-4-oxo(3-hydroquinolyl)}carbonylamino)ethyl]amino}sulfonyl)-3,5-dimethylphenoxy]butanoylamino}ethyl)carbamoyl]-2-sulfoethyl}carbamoyl)-4-aminobutanoylamino]-3-sulfopropyl}ethyl)carbomoyl]propoxy}-2,6-dimethylphenyl)sulfonyl]amino}-3-({7-[(imidazol-2-ylamino)methyl]-1-methyl-4-oxo(3-hydroquinolyl)}-carbonylamino)propanoic Acid Conjugate Bis (trifluoroacetate) could be prepared in high yield using ascorbic acid as a buffer agent, a transfer ligand and a radiolytic stabilizer. $^{177}$Lu-DOTA/(2S)-2-{[(4-{3-[N-(2-{2-[(4S)-4-(N-{1-[N-(2-{4-[4-({[(1S)-1-Carboxy-2-({7-[(imidazol-2-ylamino)methyl]-1-methyl-4-oxo(3-hydroquinolyl)}carbonylamino)ethyl]amino}sulfonyl)-3,5-dimethylphenoxy]butanoylamino}ethyl)carbamoyl]-2-sulfoethyl)carbamoyl)-4-aminobutanoylamino]-3-sulfopropyl}ethyl)carbamoyl]propoxy}-2,6-dimethylphenyl)sulfonyl]amino}-3-({7-[(imidazol-2-ylamino)methyl]-1-methyl-4-oxo(3-hydroquinolyl)}-carbonylamino)propanoic Acid Conjugate Bis (trifluoroacetate) remains stable in solution for at least 24 hours. Ascorbic acid can be used as a buffer agent, a transfer ligand, and a radiolytic stabilizer for the routine preparation and stabilization of $^{177}$Lu-labeled biomolecules.

What is claimed is:

1. A radiopharmaceutical composition comprising a radiolabeled chelator-biomolecule conjugate of the formula M-Ch-Ln-(BM)$_m$; and an amount of a compound of formula (I):

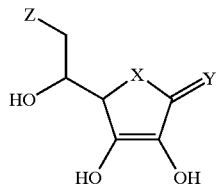

or a pharmaceutically acceptable salt thereof,
wherein
M is a metallic radioisotope;
Ch is a metal chelator;
Ln is an optional linking group;
BM is a biomolecule;
m is 1 to about 10;
X is O, NR$^1$, or CHR$^1$;
Y is O or S;
Z is hydroxyl or halogen;
R$^1$ is selected from: (C$_1$–C$_{10}$) alkyl substituted with 0–5 R$^2$, (C$_3$–C$_{10}$) cycloalkyl substituted with 0–5 R$^2$, (C$_2$–C$_{10}$) alkenyl substituted with 0–5 R$^2$, and aryl substituted with 0–5 R$^2$; and
R$^2$ is independently selected at each occurrence from: NH$_2$, OH, CO$_2$H, C(=O)NH$_2$, NHC(=NH)NH$_2$, PO$_3$H$_2$, and SO$_3$H;
wherein the concentration of the compound of formula (I) in an pharmaceutically acceptable carrier or diluent is about 2 mg/mL to about 200 mg/mL; and
wherein the amount of the compound of formula (I) is effective to: (1) stabilize the radiolabeled chelator-biomolecule conjugate of the formula M-Ch-Ln-(BM)$_m$ against radiation induced degradation and to at least one of (2) control the pH of the radiopharmaceutical composition and (3) reduce radiometal colloid formation.

2. The radiopharmaceutical composition of claim 1 wherein the amount is effective to: (1) stabilize the radiopharmaceutical against radiation induced degradation and (2) control the pH of the radiopharmaceutical.

3. The radiopharmaceutical composition of claim 1 wherein the amount is effective to: (1) stabilize the radiopharmaceutical against radiation induced degradation and (2) reduce radiometal colloid formation.

4. The radiopharmaceutical composition of claim 1 wherein the amount is effective to: (1) stabilize the radiopharmaceutical against radiation induced degradation and (2) control the pH of the radiopharmaceutical and (3) reduce radiometal colloid formation.

5. The radiopharmaceutical composition of claim 1 wherein X is O.

6. The radiopharmaceutical composition of claim 1 wherein Y is O.

7. The radiopharmaceutical composition of claim 1 wherein Z is hydroxyl.

8. The radiopharmaceutical composition of claim 1 wherein m is 1 to about 5.

9. The radiopharmaceutical composition of claim 1 wherein m is 1 or 2.

10. The radiopharmaceutical composition of claim 1 wherein m is 1.

11. The radiopharmaceutical composition of claim 1 wherein m is 1 to about 5; X is O; and Y is O.

12. The radiopharmaceutical composition of claim 1 wherein m is 1 or 2; X is O; Y is O; and Z is hydroxyl.

13. The radiopharmaceutical composition of claim 1 wherein m is 1; X is O; Y is O; and Z is hydroxyl.

14. The radiopharmaceutical composition of claim 1 wherein the metallic radioisotope is present at a level of about 10 mCi to about 2000 mCi.

15. The radiopharmaceutical composition of claim 1 wherein the metallic radioisotope is present at a concentration of greater than about 5 mCi/mL.

16. The radiopharmaceutical composition of claim 1 wherein the radiolabeled chelator-biomolecule conjugate of the formula M-Ch-Ln-(BM)$_m$ is a diagnostic radiopharmaceutical.

17. The radiopharmaceutical composition of claim 1 wherein the radiolabeled chelator-biomolecule conjugate of the formula M-Ch-Ln-(BM)$_m$, is a therapeutic radiopharmaceutical.

18. The radiopharmaceutical composition of claim 1 wherein the biomolecule is an antibody.

19. The radiopharmaceutical composition of claim 1 wherein the biomolecule is an antibody fragment.

20. The radiopharmaceutical composition of claim 1 wherein the biomolecule is a peptide.

21. The radiopharmaceutical composition of claim 1 wherein the biomolecule is a peptidomimetic.

22. The radiopharmaceutical composition of claim 1 wherein the biomolecule is a non-peptide.

23. The radiopharmaceutical composition of claim 1 wherein the biomolecule is a cyclic IIb/IIIa receptor antagonist; an RGD containing peptide; a fibrinogen receptor antagonist; a IIb/IIIa receptor ligand; a ligand for the polymerization site of fibrin; a laminin derivative; a ligand for fibrinogen; a thrombin ligand; an oligopeptide that corresponds to the IIIa protein; a hirudin-based peptide; a IIb/IIIa receptor ligand; a thrombus, platelet binding, or atherosclerotic plaque binding peptide; a fibrin binding peptide; a hirudin-based peptide; a fibrin binding protein; a guanine derivative that binds to the IIb/IIIa receptor; a tyrosine derivative; a leukocyte binding peptide; a chemotactic peptide; a leukostimulatory agent; an LTB4 antagonist; a somatostatin analog; a selectin binding peptide; a biological-function domain; a platelet factor 4 or growth factor; a compound that binds to a receptor that is expressed or upregulated in angiogenic tumor vasculature; a peptide, polypeptide or peptidomimetic that binds with high affinity to the receptors VEGF receptors Flk-1/KDR, Flt-1, or neuropilin-1; a peptide, polypeptide or peptidomimetic that binds to αvβ3, αvβ5, α5β1, α4β1, α1β1, or α2β2; a compound that interacts with receptor tyrosine kinases; a protein, antibody, antibody fragment, peptide, polypeptide, or peptidomimetic that binds to receptors or binding sites on a tissue, organ, enzyme or fluid; a β-amyloid protein that has been demonstrated to accumulate in patients with Alzheimer's disease; an atrial naturetic factor derived peptide that binds to myocardial or renal receptor; an antimyosin antibody that binds to areas of infarcted tissue; or a nitroimidazole derivative that localizes in hypoxic areas in vivo.

24. The radiopharmaceutical composition of claim 1 wherein the chelator is a cyclic or acyclic polyaminocarboxylate, a diaminedithiol, a triamidemonothiol, a monoaminemonoamidedithiol, a monoaminediamidemonothiol, a diaminedioxime, or a hydrazine.

25. The radiopharmaceutical composition of claim 1 wherein the chelator is tetradentate, with donor atoms selected from nitrogen, oxygen and sulfur.

26. The radiopharmaceutical composition of claim 1 wherein the chelator is diethylenetriaminepentaacetic acid (DTPA); 1,4,7,10-tetraazazcyclododecane-1,4,7,10-tetraacetic acid (DOTA); 1,4,8,11-tetraazazcyclo-tetradecane-1,4,8,11-tetraacetic acid (TETA); 1,4,7,10-tetraazazcyclododecane-1,4,7-triacetic acid (DO3A); 2-Benzyl-1,4,7,10-tetraazazcyclododecane-1,4,7,10-tetraacetic acid (2-Bz-DOTA); alpha-(2-phenethyl)-1,4,7,10-tetraazazcyclododecane-1-acetic-4,7,10-tris (methylacetic) acid; 2-benzyl-cyclohexyldiethylene-triaminepentaacetic acid; 2-benzyl-6-methyl-diethylenetriaminepentaacetic acid; or 6,6"-bis[N,N,N",N"-tetra(carboxymethyl)aminomethyl]-4'-(3-amino-4-methoxyphenyl)-2,2':6',2"-terpyridine.

27. The radiopharmaceutical composition of claim 1 wherein the metallic radioisotope is $^{177}$Lu, $^{149}$Pm, $^{153}$Sm, $^{166}$Ho, $^{90}$Y, $^{111}$In, $^{67}$Ga, $^{68}$Ga, $^{89}$Zr, $^{99m}$Tc, $^{117m}$Sn, $^{203}$Pb, $^{177}$Lu, $^{47}$Sc, $^{109}$Pd, $^{105}$Rh, $^{186}$Re, $^{166}$Re, $^{60}$Cu, $^{64}$Cu, $^{67}$Cu, $^{97}$Ru, or $^{212}$Bi.

28. The radiopharmaceutical composition of claim 1 wherein the metallic radioisotope is $^{99m}$Tc, $^{117m}$Sn, $^{111}$In, $^{203}$Pb, $^{67}$Ga, $^{68}$Ga, $^{89}$Zr, $^{90}$Y, $^{177}$Lu, $^{149}$Pm, $^{153}$Sm, $^{166}$Ho, $^{47}$Sc, $^{109}$Pd, $^{105}$Rh, $^{186}$Re, $^{188}$Re, $^{60}$Cu, $^{62}$Cu, $^{64}$Cu or $^{67}$Cu.

29. The radiopharmaceutical composition of claim 1 wherein the metallic radioisotope is $^{111}$In, $^{90}$Y, or $^{177}$Lu.

30. A radiopharmaceutical composition comprising a radiolabeled chelator-biomolecule conjugate of the formula M-Ch-Ln-(BM)$_m$; and a compound of formula (I):

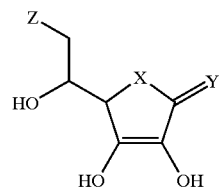

or a pharmaceutically acceptable salt thereof,
wherein
M is a metallic radioisotope;
Ch is a metal chelator;
Ln is an optional linking group;
BM is a biomolecule;
m is 1 to about 10;
X is O, NR$^1$, or CHR$^1$;
Y is O or S;
Z is hydroxyl or halogen;
R$^1$ is selected from: (C$_1$–C$_{10}$) alkyl substituted with 0–5 R$^2$, (C$_3$–C$_{10}$) cycloalkyl substituted with 0–5 R$^2$, (C$_2$–C$_{10}$) alkenyl substituted with 0–5 R$^2$, and aryl substituted with 0–5 R$^2$;
R$^2$ is independently selected at each occurrence from: NH$_2$, OH, CO$_2$H, C(=O)NH$_2$, NHC(=NH)NH$_2$, PO$_3$H$_2$, and SO$_3$H;
wherein the concentration of the compound of formula (I) in an pharmaceutically acceptable carrier or diluent is about 2 mg/mL to about 200 mg/mL; and
provided the radiopharmaceutical composition does not comprise an additional buffering agent or an additional chelating agent.

31. A method for buffering a radiopharmaceutical comprising contacting the radiopharmaceutical with an amount of a compound of formula (I):

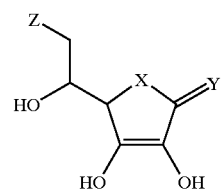

or a pharmaceutically acceptable salt thereof,
wherein
X is O, NR$^1$, or CUR$^1$;
Y is O or S;
Z is hydroxyl or halogen;
R$^1$ is selected from: (C$_1$–C$_{10}$) alkyl substituted with 0–5 R$^2$, (C$_3$–C$_{10}$) cycloalkyl substituted with 0–5 R$^2$, (C$_2$–C$_{10}$) alkenyl substituted with 0–5 R$^2$, and aryl substituted with 0–5 R$^2$;
R$^2$ is independently selected at each occurrence from: NH$_2$, OH, CO$_2$H, C(=O)NH$_2$, NHC(=NH)NH$_2$, PO$_3$H$_2$, and SO$_3$H;
wherein the concentration of the compound of formula (I) in an pharmaceutically acceptable carrier or diluent is about 2 mg/mL to about 200 mg/mL; and
wherein the amount is effective to control the pH of the radiopharmaceutical.

32. The method of claim 31 wherein the radiopharmaceutical is a radiolabeled chelator-biomolecule conjugate of the formula M-Ch-Ln-(BM)$_m$;
wherein
M is a metallic radioisotope;
Ch is a metal chelator;
Ln is an optional linking group;
BM is a biomolecule; and
m is 1 to about 10.

33. The method of claim 31 wherein the compound of formula (I) controls the pH of the radiopharmaceutical during at least one of the preparation, release, storage, and transportation of the radiopharmaceutical.

34. A method for chelating a radiopharmaceutical comprising contacting the radiopharmaceutical with an amount of a compound of formula (I):

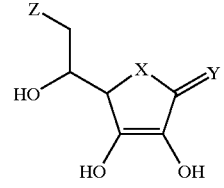

or a pharmaceutically acceptable salt thereof,
wherein
X is O, NR$^1$, or CHR$^1$;
Y is O or S;
Z is hydroxyl or halogen;
R$^1$ is selected from: (C$_1$–C$_{10}$) alkyl substituted with 0–5 R$^2$, (C$_3$–C$_{10}$) cycloalkyl substituted with 0–5 R$^2$, (C$_2$–C$_{10}$) alkenyl substituted with 0–5 R$^2$, and aryl substituted with 0–5 R$^2$;
R$^2$ is independently selected at each occurrence from: NH$_2$, OH, CO$_2$H, C(=O)NH$_2$, NHC(=NH)NH$_2$, PO$_3$H$_2$, and SO$_3$H;
wherein the concentration of the compound of formula (I) in an pharmaceutically acceptable carrier or diluent is about 2 mg/mL to about 200 mg/mL; and wherein the amount is effective to reduce radiometal colloid formation.

35. The method of claim 34 wherein the radiopharmaceutical is a radiolabeled chelator-biomolecule conjugate of the formula M-Ch-Ln-(BM)$_m$;
wherein
M is a metallic radioisotope;
Ch is a metal chelator;
Ln is an optional linking group;
BM is a biomolecule; and
m is 1 to about 10.

36. The method of claim 34 wherein the compound of formula (I) reduces radiometal colloid formation during at least one of the preparation, release, storage, and transportation of the radiopharmaceutical.

37. A method for stabilizing a radiopharmaceutical against radiation induced degradation and at least one of (1) controlling the pH of the radiopharmaceutical and (2) reducing radiometal colloid formation; comprising contacting the radiopharmaceutical with an amount of a compound of formula (I):

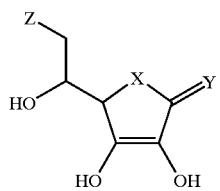

or a pharmaceutically acceptable salt thereof,
wherein
X is O, NR$^1$, or CHR$^1$;
Y is O or S;
Z is hydroxyl or halogen;
R$^1$ is selected from: (C$_1$–C$_{10}$) alkyl substituted with 0–5 R$^2$, (C$_3$–C$_{10}$) cycloalkyl substituted with 0–5 R$^2$, (C$_2$–C$_{10}$) alkenyl substituted with 0–5 R$^2$, and aryl substituted with 0–5 R$^2$;
R$^2$ is independently selected at each occurrence from: NH$_2$, OH, CO$_2$H, C(=O)NH$_2$, NHC(=NH)NH$_2$, PO$_3$H$_2$, and SO$_3$H;
wherein the concentration of the compound of formula (I) in an pharmaceutically acceptable carrier or diluent is about 2 mg/mL to about 200 mg/mL; and
wherein the amount is effective to: (1) stabilize the radiopharmaceutical against radiation induced degradation and to at least one of (2) control the pH of the radiopharmaceutical and (3) reduce radiometal colloid formation.

38. The method of claim 37 wherein the amount is effective to: (1) stabilize the radiopharmaceutical against radiation induced degradation and (2) control the pH of the radiopharmaceutical.

39. The method of claim 37 wherein the amount is effective to: (1) stabilize the radiopharmaceutical against radiation induced degradation and (2) reduce radiometal colloid formation.

40. The method of claim 37 wherein the amount is effective to: (1) stabilize the radiopharmaceutical against radiation induced degradation, (2) control the pH of the radiopharmaceutical and (3) reduce radiometal colloid formation.

41. The method of claim 37 wherein the radiopharmaceutical is a radiolabeled chelator-biomolecule conjugate of the formula M-Ch-Ln-(BM)$_m$
wherein
M is a metallic radioisotope;
Ch is a metal chelator;
Ln is an optional linking group;
BM is a biomolecule; and
m is 1 to about 10.

42. The method of claim 37 wherein the amount is effective to: (1) stabilize the radiopharmaceutical against radiation induced degradation and to at least one of (2) control the pH of the radiopharmaceutical and (3) reduce radiometal colloid formation; during at least one of the preparation, release, storage, and transportation of the radiopharmaceutical.

43. A method for preparing a stable radiopharmaceutical composition comprising contacting a radiolabeled chelator-biomolecule conjugate of the formula M-Ch-Ln-(BM)$_m$ and an amount of a compound of formula (I):

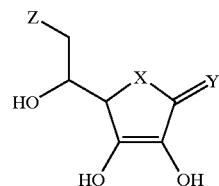

or a pharmaceutically acceptable salt thereof,
wherein
M is a metallic radioisotope;
Ch is a metal chelator;
Ln is an optional linking group;
BM is a biomolecule;
m is 1 to about 10;
X is O, NR$^1$, or CHR$^1$;
Y is O or S;
Z is hydroxyl or halogen;
R$^1$ is selected from: (C$_1$–C$_{10}$) alkyl substituted with 0–5 R$^2$, (C$_3$–C$_{10}$) cycloalkyl substituted with 0–5 R$^2$, (C$_2$–C$_{10}$) alkenyl substituted with 0–5 R$^2$, and aryl substituted with 0–5 R$^2$; and
R$^2$ is independently selected at each occurrence from: NH$_2$, OH, CO$_2$H, C(=O)NH$_2$, NHC(=NH)NH$_2$, PO$_3$H$_2$, and SO$_3$H;
wherein the concentration of the compound of formula (I) in an pharmaceutically acceptable carrier or diluent is about 2 mg/mL to about 200 mg/mL; and
wherein the amount of the compound of formula (I) is effective to: (1) stabilize the radiolabeled chelator-biomolecule conjugate of the formula M-Ch-Ln-(BM)$_m$ against radiation induced degradation and to at least one of (2) control the pH of the radiopharmaceutical composition and (3) reduce radiometal colloid formation.

44. A kit comprising a sealed vial comprising a predetermined quantity of a radiolabeled chelator-biomolecule conjugate of the formula M-Ch-Ln-(BM)$_m$, and an amount of a compound of formula (I):

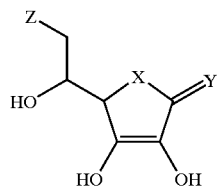

or a pharmaceutically acceptable salt thereof, wherein
M is a metallic radioisotope;
Ch is a metal chelator;
Ln is an optional linking group;
BM is a biomolecule;
m is 1 to about 10;
X is O, $NR^1$, or $CHR^1$;
Y is O or S;
Z is hydroxyl or halogen;
$R^1$ is selected from: $(C_1-C_{10})$ alkyl substituted with 0–5 $R^2$, $(C_3-C_{10})$ cycloalkyl substituted with 0–5 $R^2$, $(C_2-C_{10})$ alkenyl substituted with 0–5 $R^2$, and aryl substituted with 0–5 $R^2$; and
$R^2$ is independently selected at each occurrence from: $NH_2$, OH, $CO_2H$, $C(=O)NH_2$, $NHC(=NH)NH_2$, $PO_3H_2$, and $SO_3H$;
wherein the concentration of the compound of formula (I) in an pharmaceutically acceptable carrier or diluent is about 2 mg/mL to about 200 mg/mL; and
wherein the amount of the compound of formula (I) is effective to: (1) stabilize the radiolabeled chelator-biomolecule conjugate of the formula M-Ch-Ln-$(BM)_m$ against radiation induced degradation and to at least one of (2) control the pH of the radiopharmaceutical composition and (3) reduce radiometal colloid formation.

45. A kit comprising
(a) a first vial comprising a predetermined quantity of a radiolabeled chelator-biomolecule conjugate of the formula M-Ch-Ln-$(BM)_m$; and an amount of a compound of formula (I):

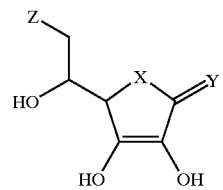

or a pharmaceutically acceptable salt thereof, wherein
M is a metallic radioisotope;
Ch is a metal chelator;
Ln is an optional linking group;
BM is a biomolecule;
m is 1 to about 10;
X is O, $NR^1$, or $CHR^1$;
Y is O or S;
Z is hydroxyl or halogen;
$R^1$ is selected from: $(C_1-C_{10})$ alkyl substituted with 0–5 $R^2$, $C_3$–C10) cycloalkyl substituted with 0–5 $R^2$, $(C_2-C_{10})$ alkenyl substituted with 0–5 $R^2$, and aryl substituted with 0–5 $R^2$; and
$R^2$ is independently selected at each occurrence from: $NH_2$, OH, $CO_2H$, $C(=O)NH_2$, $NHC(=NH)NH_2$, $PO_3H_2$, and $SO_3H$; and
wherein the amount of the compound of formula (I) is effective to: (1) stabilize the radiolabeled chelator-biomolecule conjugate of the formula M-Ch-Ln-$(BM)_m$ against radiation induced degradation and to at least one of (2) control the pH of the radiopharmaceutical composition and (3) reduce radiometal colloid formation; and
(b) a second vial comprising a pharmaceutically acceptable carrier or diluent;
wherein the compound of formula (I) is present in an amount sufficient to provide a concentration of about 2 mg/mL to about 200 mg/mL in the pharmaceutically acceptable carrier or diluent.

* * * * *

UNITED STATES PATENT AND TRADEMARK OFFICE
CERTIFICATE OF CORRECTION

PATENT NO. : 6,713,042 B2
DATED : March 30, 2004
INVENTOR(S) : Shuang Liu

It is certified that error appears in the above-identified patent and that said Letters Patent is hereby corrected as shown below:

Column 9,
Line 60, delete "89Zr," and insert -- $^{89}$Zr, --;
Line 66, delete "153Sm," and insert -- $^{153}$Sm, --;

Column 10,
Line 28, delete "z" and insert -- Z --;

Column 26,
Line 5, delete "(3-sulfo-$^{2}$-{$^{2}$-[1,4,7,10-" and insert -- (3-sulfo-2-{2-[1,4,7,10- --;
Line 8, delete "phenyl}sulfonyl)amino]-$^{3}$-" and insert -- phenyl}sulfonyl)amino]-3- --;

Column 28,
Line 12, delete "DOTAI" and insert -- DOTA/ --;
Line 15, delete "-carbonyl amino)" and insert -- -carbonylamino) --;
Line 16, delete "-40amino" and insert -- -4-amino --;

Column 33,
Line 34, delete "in an pharmaceutically acceptable" and insert -- in a pharmaceutically acceptable --.

Column 38,
Line 54, delete "in an pharmaceutically acceptable" and insert -- in a pharmaceutically acceptable --;

Column 39,
Line 30, delete "in an pharmaceutically acceptable" and insert -- in a pharmaceutically acceptable --.

Signed and Sealed this

Twelfth Day of October, 2004

JON W. DUDAS
*Director of the United States Patent and Trademark Office*

SEQUENCE LISTING

<160> NUMBER OF SEQ ID NOS: 11

<210> SEQ ID NO 1
<211> LENGTH: 16
<212> TYPE: PRT
<213> ORGANISM: Artificial Sequence -continued

```
<220> FEATURE:
<223> OTHER INFORMATION: Synthetic construct

<400> SEQUENCE: 1

Met Trp Tyr Arg Pro Asp Leu Asp Glu Arg Lys Gln Gln Lys Arg Glu
1               5                   10                  15

<210> SEQ ID NO 2
<211> LENGTH: 18
<212> TYPE: PRT
<213> ORGANISM: Artificial Sequence
<220> FEATURE:
<223> OTHER INFORMATION: Synthetic construct

<400> SEQUENCE: 2

Ala Gln Leu Ala Gly Glu Cys Arg Glu Asn Val Cys Met Gly Ile Glu
1               5                   10                  15

Gly Arg

<210> SEQ ID NO 3
<211> LENGTH: 8
<212> TYPE: PRT
<213> ORGANISM: Artificial Sequence
<220> FEATURE:
<223> OTHER INFORMATION: Synthetic construct

<400> SEQUENCE: 3

Ala Pro Ser Gly His Tyr Lys Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic construct

<400> SEQUENCE: 4

Lys Arg Thr Gly Gln Tyr Lys Leu
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic construct

<400> SEQUENCE: 5

Arg Gly Asp Arg Gly Asp
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic construct

<400> SEQUENCE: 6

Arg Gly Asp Arg Gly Asp Asp
1               5

<210> SEQ ID NO 7
<211> LENGTH: 6
<212> TYPE: PRT
```

```
<213> ORGANISM: Artificial Sequence
<220> FEATURE:
<223> OTHER INFORMATION: Synthetic construct

<400> SEQUENCE: 7

Arg Gly Asp Arg Gly Asp
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Mamb linkage

<400> SEQUENCE: 8

Ala Arg Gly Asp
1

<210> SEQ ID NO 9
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(7)
<223> OTHER INFORMATION: BTD linkage

<400> SEQUENCE: 9

Arg Gly Asp Val Gly Ser Ser Gly Val Ala
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic construct

<400> SEQUENCE: 10

Cys Asp Cys Arg Gly Asp Cys Phe Cys
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic construct

<400> SEQUENCE: 11

Cys Asn Gly Asp Cys
1               5
```